US011590091B2

(12) United States Patent
Garrido Suárez et al.

(10) Patent No.: US 11,590,091 B2
(45) Date of Patent: Feb. 28, 2023

(54) FIXED DOSE COMPOSITION OF PARACETAMOL: AMITRIPTYLINE AND METHOD FOR THE TREATMENT OF MIXED CANCER PAIN

(71) Applicant: CENTRO DE INVESTIGACIÓN Y DESARROLLO DE MEDICAMENTOS CIDEM, Havana (CU)

(72) Inventors: Bárbara Beatriz Garrido Suárez, Havana (CU); Addis Bellma Menéndez, Havana (CU); Ania González Cortezón, Havana (CU); Nilia De La Paz Martín-Viaña, Havana (CU); Pedro Gilberto Bárzaga Fernández, Havana (CU); Rolando Perdomo Morales, Havana (CU); Alejandro Saúl Padrón Yaquis, Havana (CU)

(73) Assignee: CENTRO DE INVESTIGACIÓN Y DESARROLLO DE MEDICAMENT, Havana (CU)

( * ) Notice: Subject to any disclaimer, the term of this patent is extended or adjusted under 35 U.S.C. 154(b) by 0 days.

(21) Appl. No.: 17/052,578

(22) PCT Filed: May 3, 2019

(86) PCT No.: PCT/CU2019/050002
§ 371 (c)(1),
(2) Date: Nov. 3, 2020

(87) PCT Pub. No.: WO2019/210889
PCT Pub. Date: Nov. 7, 2019

(65) Prior Publication Data
US 2021/0236440 A1    Aug. 5, 2021

(30) Foreign Application Priority Data
May 3, 2018    (CU) .................................. 2018-0037

(51) Int. Cl.
*A61K 31/167*    (2006.01)
*A61K 31/135*    (2006.01)
*A61K 45/06*    (2006.01)
*A61K 9/00*    (2006.01)
*A61P 25/04*    (2006.01)
*A61P 29/00*    (2006.01)

(52) U.S. Cl.
CPC .......... *A61K 31/167* (2013.01); *A61K 9/0053* (2013.01); *A61K 31/135* (2013.01); *A61K 45/06* (2013.01); *A61P 25/04* (2018.01); *A61P 29/00* (2018.01)

(58) Field of Classification Search
CPC .. A61K 31/135; A61K 31/167; A61K 9/0053; A61P 25/00; A61P 25/04; A61P 29/00
See application file for complete search history.

(56) References Cited

U.S. PATENT DOCUMENTS

2005/0256182 A1* 11/2005 Sutter .................. A61K 31/405
514/419
2008/0138422 A1* 6/2008 Staniforth ............... A61P 25/02
424/489

FOREIGN PATENT DOCUMENTS

WO    2005077168 A1    8/2005
WO    2014095088 A1    6/2014

OTHER PUBLICATIONS

Garg, J. Anesthes. & Crit. Care, publ. 2016, MedCrave, vol. 4(3), pp. 1-3 (Year: 2016).*
Bray, Freddie, et al. "Global Cancer Transitions According to the Human Development Index (2008-2030): A Population-Based Study." The Lancet Oncology 13.8 (2012): 790-801.
Breivik, H., et al. "Cancer-Related Pain: A Pan-European Survey of Prevalence, Treatment, and Patient Attitudes." Annals of Oncology 20.8 (2009): 1420-1433.
Hershman, Dawn L., et al. "Prevention and Management of Chemotherapy-Induced Peripheral Neuropathy in Survivors of Adult Cancers: American Society of Clinical Oncology Clinical Practice Guideline." J Clin Oncol 32.18 (2014): 1941-1967.
Cata J.P., et al., "Mechanisms of Chemotherapy-Induced Neuropathic Pain." In: Paice JA, Bell RF, Kalso EA, Soyannwo OA, editors. Cancer Pain from Molecules to Suffering. Seattle: IASP Press; 2010. p. 3-21 (Libra se puede imprimir el capítulo) (Libra se puede imprimir el capítulo.
Bennett NI. Treatment of Cancer Pain. In: Tracey I editor IASP Refresher Courses on Pain Management 2012, IASP Press, Seattle, p. 301-304 (Libra se puede imprimir el capítulo).
Urch, C. E., et al., "Neuropathic Pain in Cancer." European Journal of Cancer 44.8 (2008): 1091-1096.
Bennett, Michael I., et al. "Prevalence and Aetiology of Neuropathic Pain in Cancer Patients: A Systematic Review." Pain 153.2 (2012): 359-365.
Bordet, Thierry, et al., "Targeting Neuroprotection as an Alternative Approach to Preventing and Treating Neuropathic Pain." Neurotherapeutics 6.4 (2009): 648-662.

(Continued)

*Primary Examiner* — Sarah Pihonak
(74) *Attorney, Agent, or Firm* — Hoffmann & Baron, LLP

(57) ABSTRACT

The present invention describes a pharmaceutical composition at a fixed dose of paracetamol and specifically amitriptyline supported by the pharmacological interaction and safety studies that show its synergy for the anti-allodynic, the mechanical anti-hypernociceptive effects and for the reduction of persistent pain, proportions, safety and neuroprotective capacity. This is aimed to the treatment of mixed pain due to cancer that can be incorporated as another option in the strategy of the WHO analgesic ladder at step 1 for the treatment of mild pain. However, it can also be included in higher steps associated with opioids for the treatment of pain of greater intensity and potentially decrease the escalation of its doses and adverse effects such as tolerance and hyperalgesia.

11 Claims, 13 Drawing Sheets

(56) References Cited

OTHER PUBLICATIONS

Sullivan, Mark D., et al., "Opioid Therapy for Chronic Pain in the United States: Promises and Perils." PAIN® 154 (2013): S94-S100.

Rivat, Cyrili, et al., "The Dark Side of Opioids in Pain Management: Basic Science Explains Clinical Observation." Pain Reports 1.2 (2016).

Latremoliere, Alban, et al., "Central Sensitization: A Generator of Pain Hypersensitivity by Central Neural Plasticity" The Journal of Pain 10.9 (2009): 895-926.

De Leo, Joyce A., et al., "The Tetrapartite Synapse: Path to CNS Sensitization and Chronic Pain." Pain 122.1 (2006): 17-21.

Tsuda, Makoto, et al. "P2X 4 Receptors Induced in Spinal Microglia Gate Tactile Allodynia After Nerve Injury." Nature 424.6950 (2003): 778-783.

Gordon-Williams, et al., "Central Neuronal Mechanisms in Cancer-Induced Bone Pain." Current Opinion in Supportive and Palliative Care 1.1 (2007): 6-10.

Peters, Christopher M., et al. "Tumor-Induced Injury of Primary Afferent Sensory Nerve Fibers in Bone Cancer Pain." Experimental Neurology 193.1 (2005): 85-100.

Yanagisawa, Yoshikazu, et al. "Bone Cancer Induces a Unique Central Sensitization Through Synaptic Changes in a Wide Area of the Spinal Cord." Molecular Pain 6 (2010): 1744-8069.

Bennett, Michael I. "Effectiveness of Antiepileptic or Antidepressant Drugs When Added to Opioids for Cancer Pain: Systematic Review" Palliative Medicine 25.5 (2011): 553-559.

Fishbain, David, "Evidence-Based Data on Pain Relief with Antidepressants." Annals of Medicine 32.5 (2000): 305-316.

Klepstad, PA, et al., "Pain and Pain Treatments in European Palliative Care Units. A Cross Sectional Survey from the European Association for Palliative Care Research Network." Palliative Medicine 19.6 (2005): 477-484.

Mayer, David J., et al. "Cellular Mechanisms of Neuropathic Pain, Morphine Tolerance, and Their Interactions." Proceedings of the National Academy of Sciences 96.14 (1999): 7731-7736.

Tawfik, V., et al., "Modulating Glial Activation in Opioid Tolerance and Neuropathic Pain: A Role for Glutamate Transporters." (2006).

Atkinson, Timothy J., et al. "Medication Pain Management in the Elderly: Unique and Underutilized Analgesic Treatment Options." Clinical Therapeutics 35.11 (2013): 1669-1689.

Gilron, Ian, et al., "Combination Pharmacotherapy for Management of Chronic Pain: From Bench to Bedside." The Lancet Neurology 12.11 (2013): 1084-1095.

Mitchell, Duncan, et al. "Antihypernociceptive Synergy Between Ibuprofen, Paracetamol and Codeine in Rats." European Journal of Pharmacology 642.1-3 (2010): 86-92.

Björkman, R., et al. "Acetaminophen Blocks Spinal Hyperalgesia Induced by NMDA and Substance P." Pain 57.3 (1994): 259-264.

Hama, Aldric T., et al., "Cannabinoid Receptor-Mediated Antinociception with Acetaminophen Drug Combinations in Rats with Neuropathic Spinal Cord Injury Pain." Neuropharmacology 58.4-5 (2010): 758-766.

Dani, Mélina, et al. "The Local Antinociceptive Effects of Paracetamol in Neuropathic Pain are Mediated by Cannabinoid Receptors." European Journal of Pharmacology 573.1-3 (2007): 214-215.

Micó, Juan A., et al. "Antidepressants and Pain." Trends in Pharmacological Sciences 27.7 (2006): 348-354.

Arsenault, Andre, et al., "Perisurgical Amitriptyline Produces a Preventive Effect on Afferent Hypersensitivity Following Spared Nerve Injury." Pain 146.3 (2009): 308-314.

Tai, Yueh-Hua, et al. "Amitriptyline Suppresses Neuroinflammation and Up-Regulates Glutamate Transporters in Morphine-Tolerant Rats." Pain 124.1-2 (2006): 77-86.

Yaron, Ilana, et al. "Fluoxetine and Amitriptyline Inhibit Nitric Oxide, Prostaglandin E2, and Hyaluronic Acid Production in Human Synovial Cells and Synovial Tissue Cultures." Arthritis & Rheumatism: Official Journal of the American College of Rheumatology 42.12 (1999): 2561-2568.

Lima, Flávia Oliveira, et al. "Direct Blockade of Inflammatory Hypernociception by Peripheral A1 Adenosine Receptors: Involvement of the NO/cGMP/PKG/KATP Signaling Pathway." PAIN® 151.2 (2010): 506-515.

Sawynok, Jana, et al., "Peripheral Antinociceptive Action of Amitriptyline in the Rat Formalin Test: Involvement of Adenosine." Pain 80.1-2 (1999): 45-55.

Treede, R-D., et al. "Neuropathic Pain: Redefinition and a Grading System for Clinical and Research Purposes." Neurology 70.18 (2008): 1630-1635.

Clauw, DJ, et al., Fibromyalgia. In: Mayer EA and Bushnell MC ed: Functional Pain Syndromes: Presentation and Pathophysiology. Seattle, IASP Press, 2009, pp. 3-22 (Fotocopia del texto).

Harano, N., et al. "Differences Between Orofacial Inflammation and Cancer Pain." Journal of Dental Research 89.6 (2010): 615-620.

Okuda, Kazuhiro, et al. "Characterization of Nociceptive Responses and Spinal Releases of Nitric Oxide Metabolites and Glutamate Evoked by Different Concentrations of Formalin in Rats." Pain 92.1-2 (2001): 107-115.

Coderre, Terence J., et al., "Central nervous System Plasticity in the Tonic Pain Response to Subcutaneous Formalin Injection" Brain Research 535.1 (1990): 155-158.

Dubuisson, David, et al., "The Formalin Test: A Quantitative Study of the Analgesic Effects of Morphine, Meperidine, and Brain Stem Stimulation in Rats and Cats." Pain 4 (1977): 161-174.

Omote, Keiichi, et al. "Formalin-Induced Nociception Activates a Monoaminergic Descending Inhibitory System." Brain Research 814.1-2 (1998): 194-198.

Densmore, Valarie S., et al. "Above-Level Mechanical Hyperalgesia in Rats Develops After Incomplete Spinal Cord Injury but not after Cord Transection, and is Reversed by Amitriptyline, Morphine and Gabapentin." Pain 151.1 (2010): 184-193.

Sawynok, Jana, et al., "Antinociception by Tricyclic Antidepressants in the Rat Formalin Test: Differential Effects on Different Behaviours Following Systemic and Spinal Administration." Pain 93.1 (2001): 51-59.

Lee, Yun-Sil, et al. "Acetaminophen Selectively Suppresses Peripheral Prostaglandin E2 Release and Increases COX-2 Gene Expression in a Clinical Model of Acute Inflammation." Pain 129.3 (2007): 279-286.

Mallet, Christophe, et al. "Endocannabinoid and Serotonergic Systems are Needed for Acetaminophen-Induced Analgesia." Pain 139.1 (2008): 190-200.

Kerckhove, Nicolas, et al. "Cav3. 2 Calcium Channels: The key Protagonist in the Supraspinal Effect of Paracetamol." PAIN® 155.4 (2014): 764-772.

Im, Kyong-Shil, et al. "The Antinociceptive Effect of Acetaminophen in a Rat Model of Neuropathic Pain." The Kaohsiung Journal of Medical Sciences 28.5 (2012): 251-258.

Harvey, William F., et al., "Pharmacologic Intervention for Osteoarthritis in Older Adults." Clinics in Geriatric Medicine 26.3 (2010): 503-515.

Finnerup, N. B., et al., Pharmacotherapy for Neuropathic Pain in Adults: A Systematic Review and Meta-Analysis. The Lancet Neurology, 14(2), (2015) 162-173.

Kontinen, V. K., et al., Predictive Validity of Neuropathic Pain Models in Pharmacological Studies with a Behavioral Outcome in the Rat: A Systematic Review. In World Congress on Pain, pp. 489-498 (2003) IASP Press.

De Vry, Jean, et al. "Pharmacological Characterization of the Chronic Constriction Injury Model of Neuropathic Pain." European Journal of Pharmacology 491.2-3 (2004): 137-148.

Benbouzid Malika, et al., "Chronic, but not Acute, Tricyclic Antidepressant Treatment Alleviates Neuropathic Allodynia After Sciatic Nerve Cuffing in Mice." European Journal of Pain 12.8 (2008): 1008-1017.

Suzuki, Rie, et al., "Bad News from the Brain: Descending 5-HT Pathways that Control Spinal Pain Processing." Trends in Pharmacological Sciences 25.12 (2004): 613-617.

Jensen, Troels S., et al., "Translation of Symptoms and Signs into Mechanisms in Neuropathic Pain." Pain 102.1 (2003): 1-8.

(56) References Cited

OTHER PUBLICATIONS

Ramer, Matt S., et al., "Wallerian Degeneration is Required for Both Neuropathic Pain and Sympathetic Sprouting Into the DRG." Pain 72.1-2 (1997): 71-78.
Berger, Julie V., et al., "Cellular and Molecular Insights Into Neuropathy-Induced Pain Hypersensitivity for Mechanism-Based Treatment Approaches." Brain Research Reviews 67 1-2 (2011): 282-310.
Dubový, Petr, "Wallerian Degeneration and Peripheral Nerve Conditions for Both Axonal Regeneration and Neuropathic Pain Induction." Annals of Anatomy-Anatomischer Anzeiger 193.4 (2011): 267-275.
Üçeyler, Nurcan, et al., "Wallerian Degeneration and Neuropathic Pain." Drug Discovery Today: Disease Mechanisms 3.3 (2006): 351-356. DOI: 10.1016/j.ddmec.2006.09.004.
Nagano, Masatoshi, et al. "Decreased Expression of Glial Cell Line-Derived Neurotrophic Factor Signaling in Rat Models of Neuropathic Pain." British Journal of Pharmacology 140.7 (2003): 1252-1260.
Griffin, J. W., "The Roles of Growth Factors in Painful Length-Dependent Axonal Neuropathies." Emerging Strategies for the Treatment of Neuropathic Pain. IASP Press, Seattle, WA, 2006. 271-290.
Austin, Paul J., et al., "The Neuro-Immune Balance in Neuropathic Pain: Involvement of Inflammatory Immune Dells, Immune-Like Glial Cells and Cytokines." Journal of Neuroimmunology 229.1-2 (2010): 26-50.
Bennett, Gary J., et al., "A Peripheral Mononeuropathy in Rat that Produces Disorders of Pain Sensation like those Seen in Man." Pain 33.1 (1988): 87-107.
Chaplan, Sandra R., et al. "Quantitative Assessment of Tactile Allodynia in the Rat Paw." Journal of Neuroscience Methods 53.1 (1994): 55-63.
Cunha, T. M., et al., "An Electronic Pressure-Meter Nociception Paw Test for Mice." Brazilian Journal of Medical and Biological Research 37.3 (2004): 401-407.
Rosland, Jan Henrik, et al., "Diazepam Attenuates Morphine Antinociception Test-Dependently in Mice." Pharmacology & Toxicology 66.5 (1990): 382-386.

Devor, Marshall, et al., "Reversible Analgesia, Atonia, and Loss of Consciousness on Bilateral Intracerebral Microinjection of Pentobarbital." Pain 94.1 (2001): 101-112.
Tallarida, Ronald J., "Quantitative Methods for Assessing Drug Synergism." Genes & Cancer 2.11 (2011): 1003-1008.
Raffa, Robert B., et al., "The Determination and Application of Fixed-Dose Analgesic Combinations for Treating Multimodal Pain." The Journal of Pain 11.8 (2010): 701-709.
Argüelles, Carlos F., et al., "Peripheral Antinociceptive Action of Morphine and the Synergistic Interaction with Lamotrigine." Anesthesiology: The Journal of the American Society of Anesthesiologists 96.4 (2002): 921-925.
Caram-Salas, Nadia L., et al. "Thiamine and Cyanocobalamin Relieve Neuropathic Pain in Rats: Synergy with Dexamethasone." Pharmacology 77.2 (2006): 53-62.
Sudoh, Yukari, et al. "Neurologic and Histopathologic Evaluation after High-Volume Intrathecal Amitriptyline." Regional Anesthesia & Pain Medicine 29.5 (2004): 434-440.
Bonnefont, Jérôme, et al. "Spinal 5-HT1A Receptors Differentially Influence Nociceptive Processing According to the Nature of the Noxious Stimulus in Rats: Effect of WAY-100635 on the Antinociceptive Activities of Paracetamol, Venlafaxine and 5-HT." Pain 114.3 (2005): 482-490.
Berger, A., et al. "Use of Antiepileptics and Tricyclic Antidepressants in Cancer Patients with Neuropathic Pain." European Journal of Cancer Care 15.2 (2006): 138-145.
Frost, Charlotte Ørsted, et al., "Bone Pain: Current and Future Treatments." Current Opinion in Pharmacology 28 (2016): 31-37.
Santos, Alysson Bo, et al., "Neuropathic Pain in a Patient with Porphyria. Case Report." Brazilian Journal of Anesthesiology 60.6 (2010): 634-638.
Soeberg B., et al., "755 Treatment of Acute Neuropathic Pain Following Iatrogenic Spinal Root Avulsion." European Journal of Pain 10.S1 (2006): S196c-S197.
Droney, Joanne, et al., "Status Epilepticus in a Hospice Inpatient Setting." Journal of Pain and Symptom Management 36.1 (2008): 97-105.

* cited by examiner

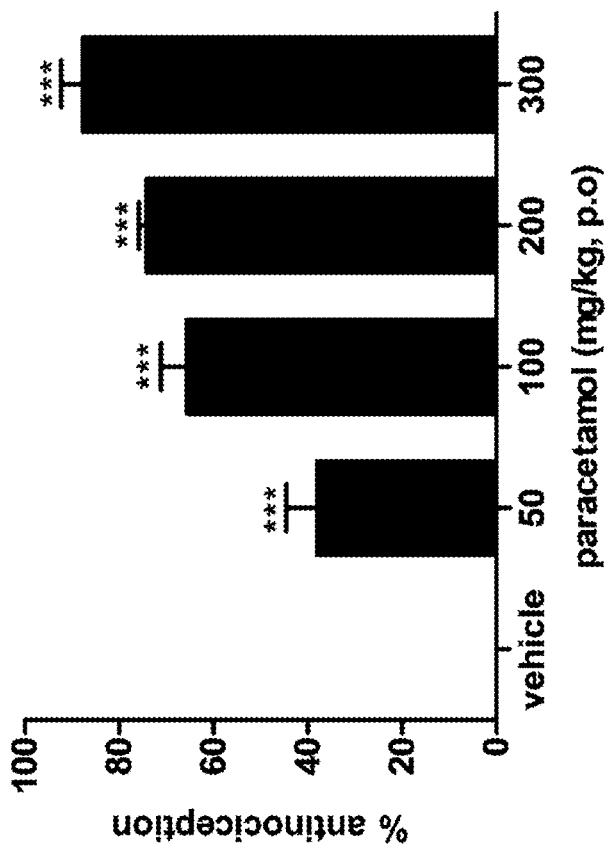
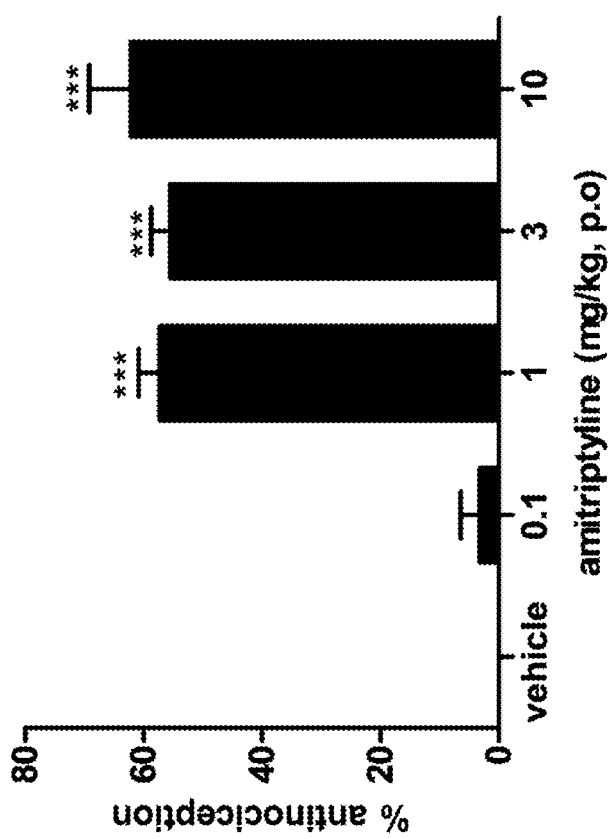
Fig.3. (A) and (B) *** $p < 0.001$ against group treated with vehicle. One-way ANOVA followed by the Tukey post hoc test.

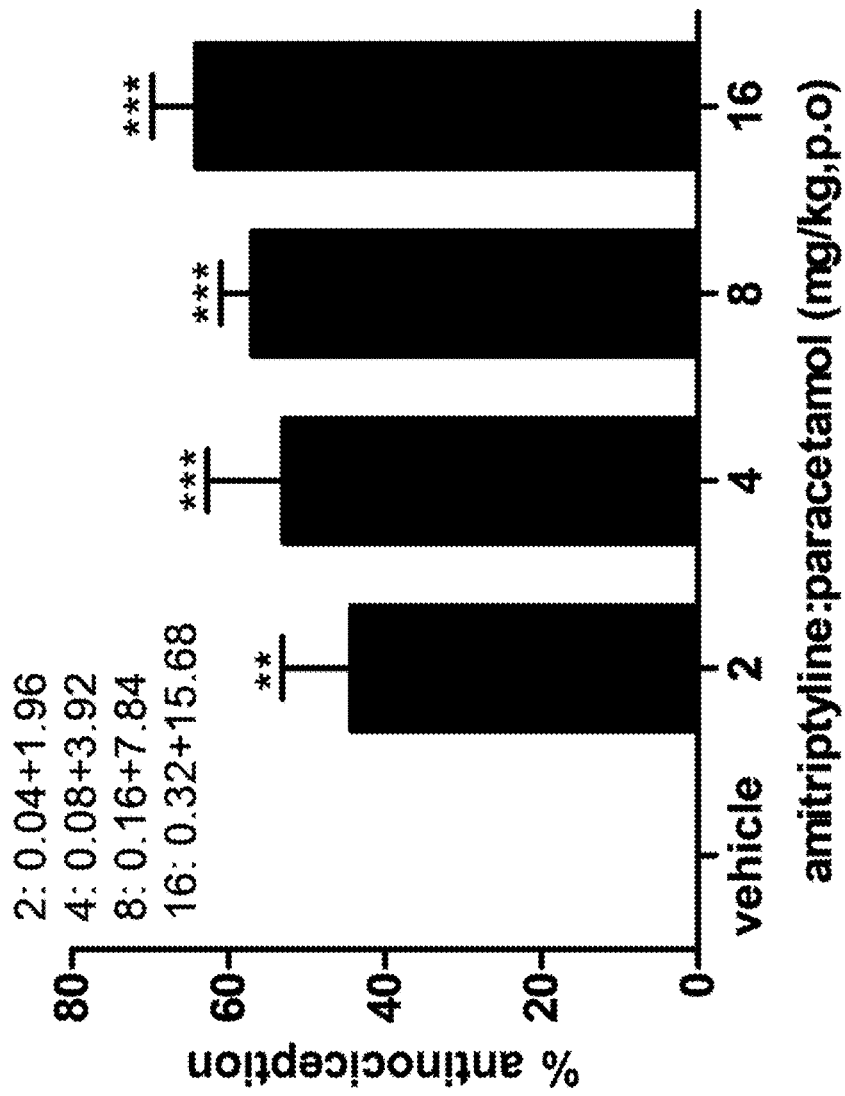
Fig.4.  p <0.01, * p <0.001 against group treated with vehicle. One-way ANOVA followed by the Tukey post hoc test.

Fig.6. (A) and (B) * p <0.05,  p <0.01, * p <0.001 against group treated with vehicle ### p <0.001 against Sham CCI group. One-way ANOVA followed by the Dunnett's post hoc test.

Fig.7. (A) and (B) * p <0.05,  p <0.01, * p <0.001 against group treated with vehicle ### p <0.001 against Sham CCI group. One-way ANOVA followed by Dunnett's post hoc test.

Fig.8. (A) and (B) * p <0.05,  p <0.01, * p <0.001 against vehicle-treated group (one-way ANOVA followed by Dunnett's post hoc test).

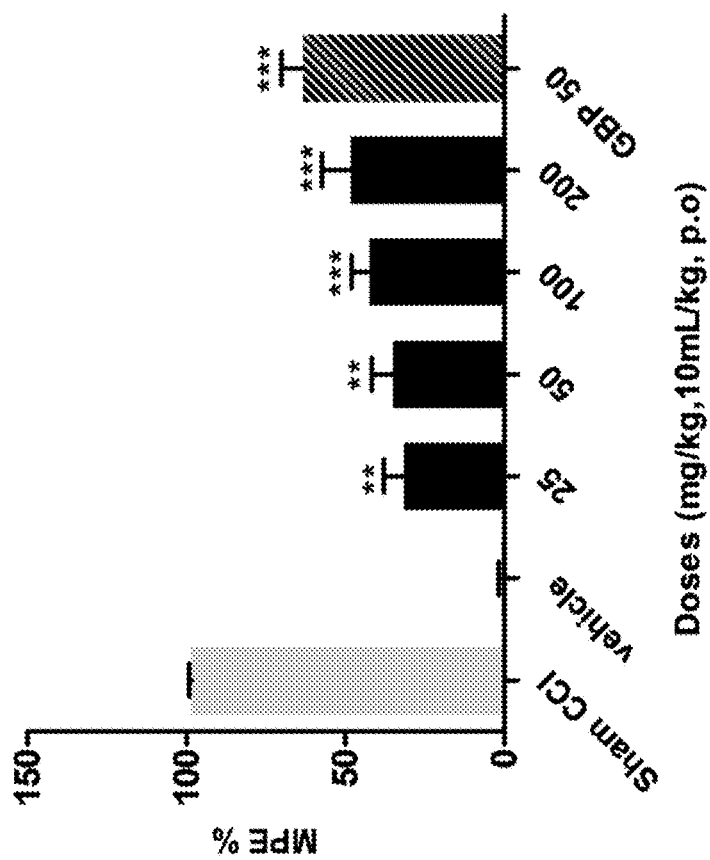
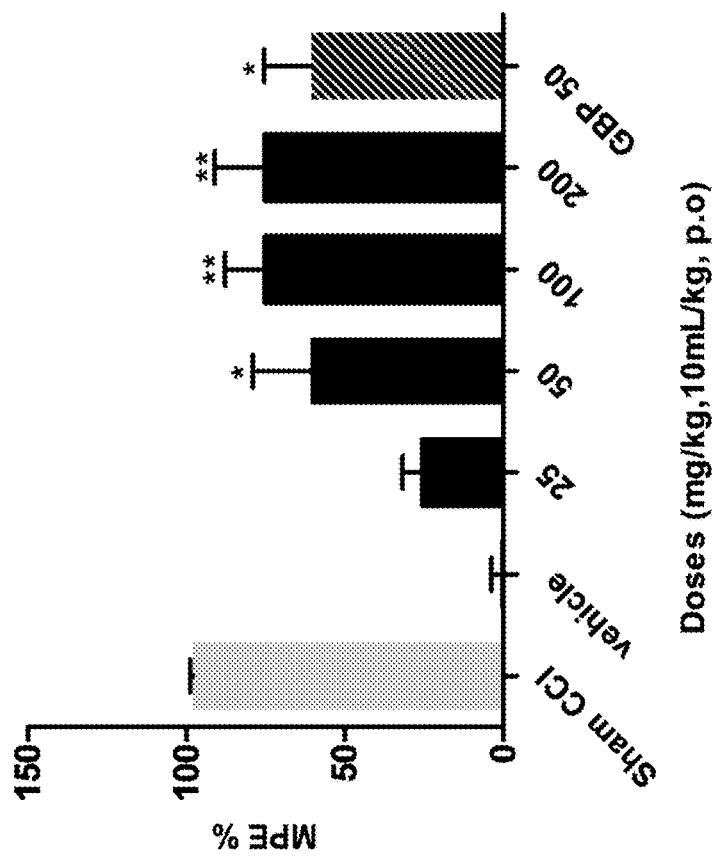
Fig.9. (A) and (B) * p <0.05,  p <0.01, * p <0.001 against group treated with vehicle. One-way ANOVA followed by Dunnett's post hoc test).

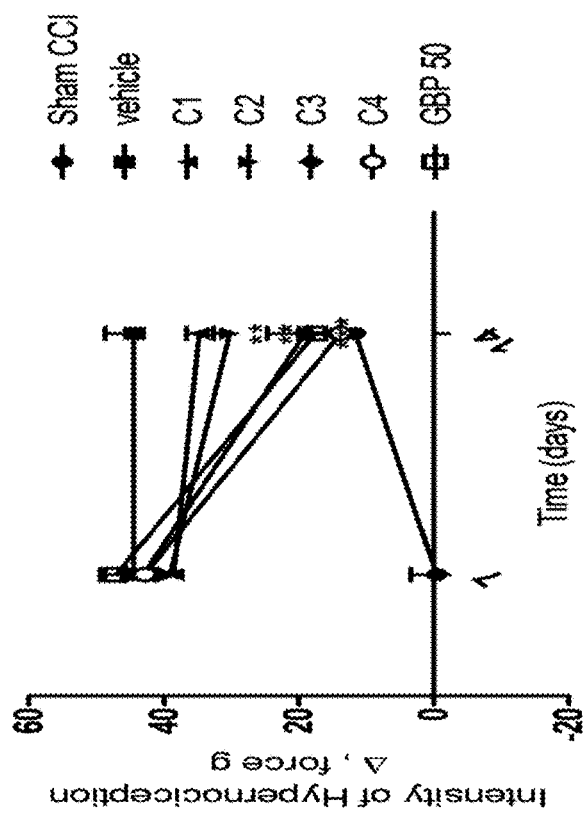
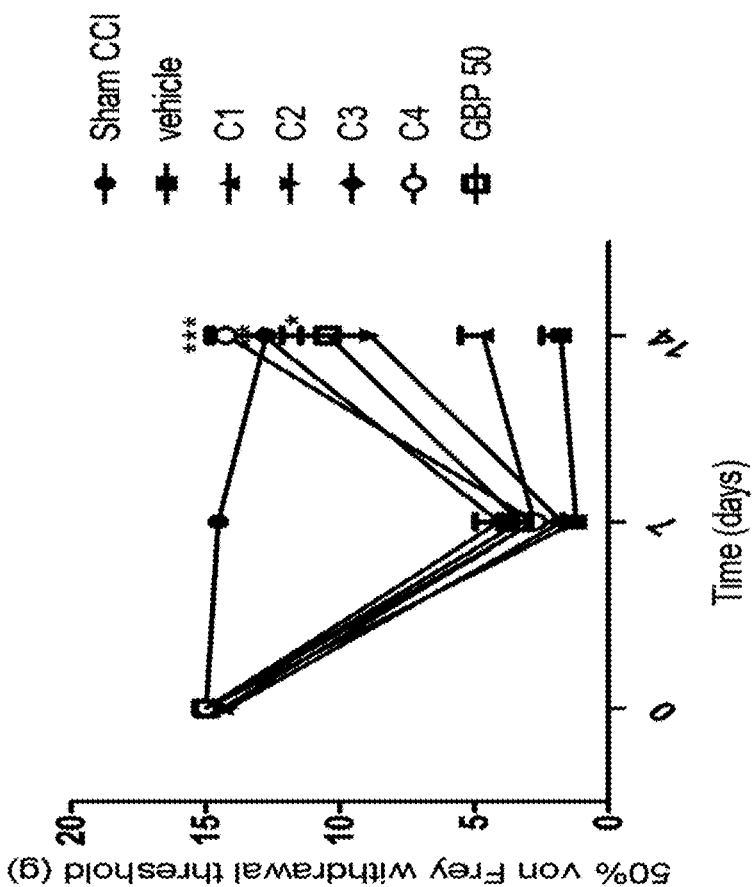
Fig. 10. A) and (B) * p <0.05,  p <0.01, * p <0.001 against group treated with vehicle ### p <0.001 represent significant differences with respect to the Sham CCI group. One-way ANOVA followed by Dunnett's post hoc test).

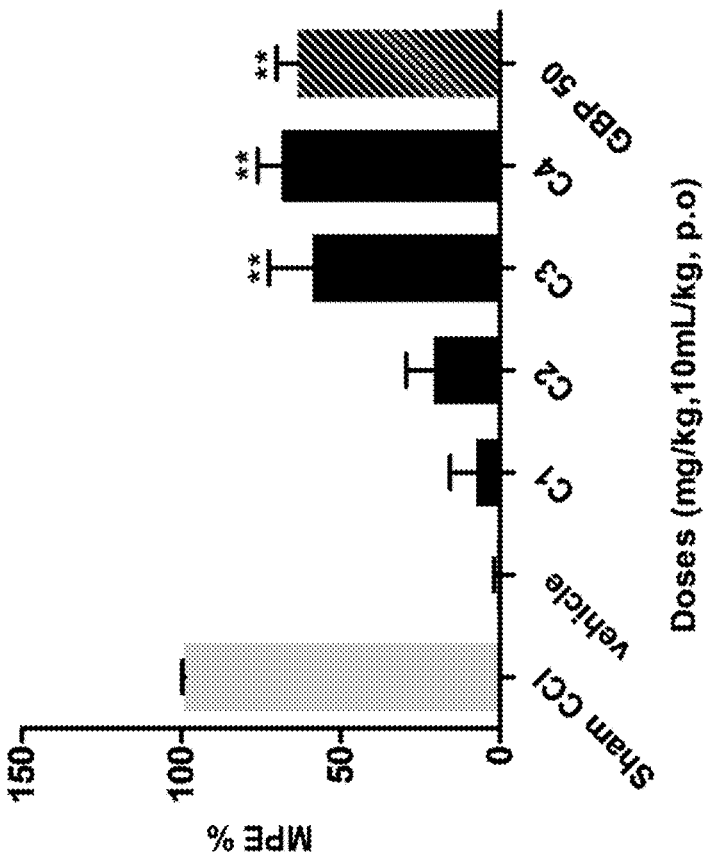
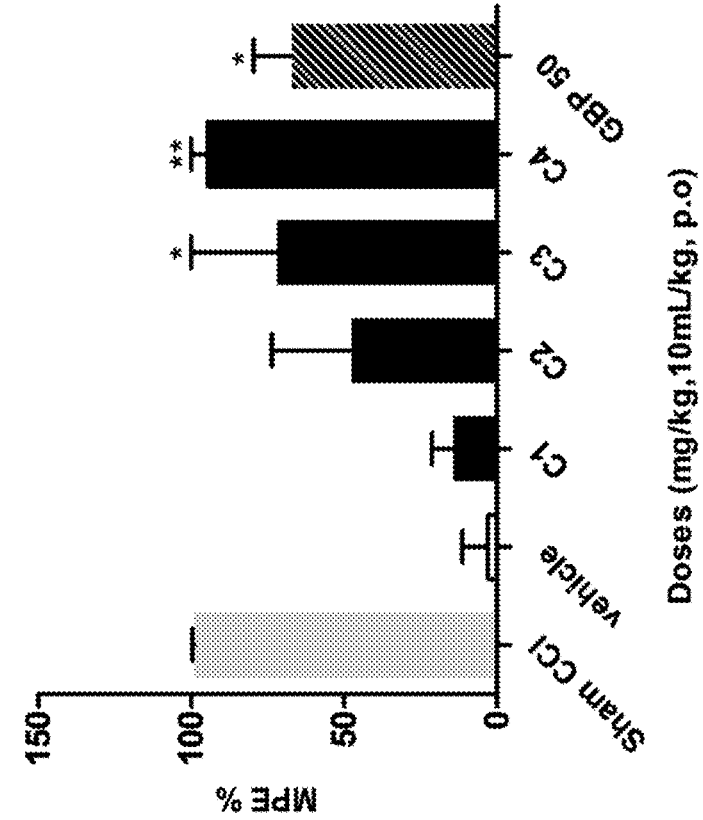
Fig.11. (A) and (B) * p <0.05,  p <0.01, * p <0.001 against group treated with vehicle. One-way ANOVA followed by Dunnett's post hoc test.).

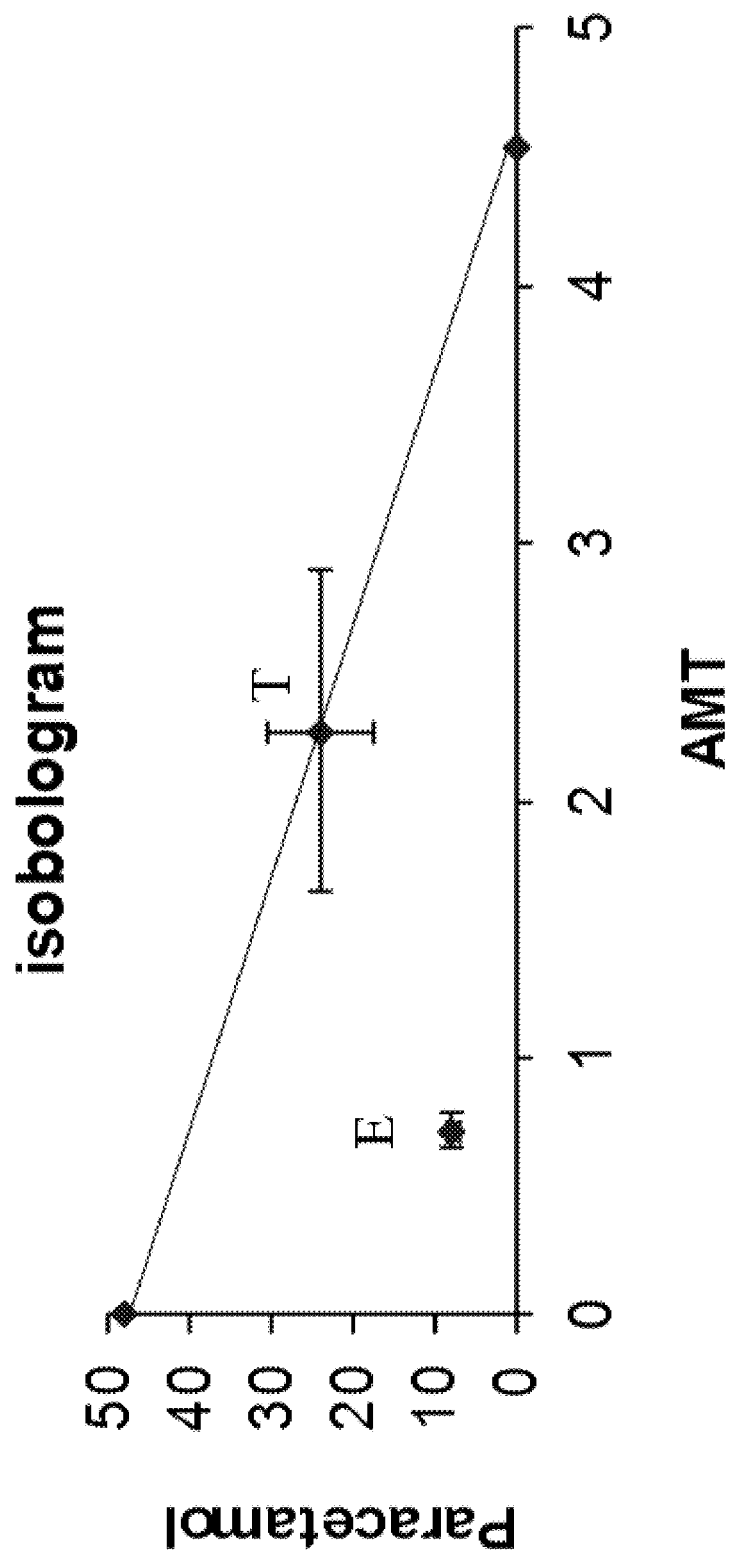

FIXED DOSE COMPOSITION OF PARACETAMOL: AMITRIPTYLINE AND METHOD FOR THE TREATMENT OF MIXED CANCER PAIN

This application is the U.S. National Phase of, and Applicant claims priority from, International Patent Application Number PCT/CU2019/050002 filed 3 May 2019, which claims priority from CU 2018-0037 filed 3 May 2018, each of which is incorporated herein by reference.

BACKGROUND OF THE INVENTION

Despite significant advances in the knowledge of cancer and the increment of survival of the affected patients, its incidence and mortality continue to rise globally. In 2008, 12.7 million new cases were reported for a total of 7.6 million cancer deaths worldwide and this number is forecast to double by 2030 with 21.4 million new cases and 13.2 million deaths. Regardless of the development achieved in the therapies directed to the tumor and the use of analgesics, in general 70% of cancer patients suffer pain, in early stages 48% and in the advanced stages between 64-75%. Its prevalence varies according to the location, in tumors of the head and neck it is very high 70%, lung and bronchi 55%, breast 54%, gynecological 60%, urogenital 52%, gastrointestinal 59%. In addition, pain from cancer can be directly related to the primary and/or metastatic tumor which infiltrates and compresses visceral, somatic and nervous structures, but also its therapeutic, whether surgical, radiotherapy or chemotherapy. Chemotherapy is one of the most commonly used and in general 3 pain syndromes related to the chemotherapeutic treatment of cancer are recognized: Arthralgias induced by aromatase inhibitors with a prevalence of 23-47%, oral mucositis induced by anti-metabolites, anti-mitotic agents, DNA-Interactives and also radiotherapy with a prevalence of 5-40%, but the most complex is the chemotherapy-induced painful peripheral neuropathy (CIPN). This form includes a neural lesion in which alterations of the mitochondrial bioenergetics, glutamatergic dysfunction and neuroinflammation have been involved. The CIPN is presented as a side effect of the 6 major agents used in cancer therapy, limiting the number of sessions that the patient receives and their chance of healing. Its incidence varies depending on the agent, the classic vinca alkaloids (25-65%), taxanes (7-50%), platinum derivatives (10-50%), thalidomide (9-41%) and the new agents, epothilones (6-71%) and bortezomid (~50%). Consequently, cancer pain can be considered as mixed where inflammatory, neuropathic and ischemic mechanisms that affect more than one site underlie, so that it can not be circumscribed as a somatic, visceral or neuropathic type strictly (Bray, E. et al. al., 2012. *Lancet Oncol*, 13: 790-801, Breivik, H. et al, 2009. *Ann, Oncol* 20: 1420-33, Hershman, D L et al, 2014. *J. Clin. Oncol*. 32: 1941-67; Cata, J P et al., 2010. In: Paice, J A, Bell, R F, Kalso, E A, Soyannwo, O A editors, *Cancer pain from molecules to suffering*, Seattle: IASP Press, p. 3-21). Consequently, antidepressants and antiepileptics offer benefit to a third of patients and are used as adjuvants in combination with non-steroidal anti-inflammatory analgesics (NSAIDs) and opioids, included in the World Health Organization analgesic ladder's (WHO analgesic ladder) own dynamic concept. Unfortunately, in Cuba there are no systematic epidemiological studies of pain, but regional and hospital studies that show similar results extrapolated to the national situation that allow cancer pain to be recognized as a health problem not only because of its high prevalence but also because of the partial ineffectiveness of the available therapies. At present, there are seven approaches for its integral management: educational interventions to provide explanations, increase the painful threshold (with social support, activity, improvement of mood, quality of sleep), modify the pathological process (chemotherapy, radiotherapy, hormonal therapy, surgical orthopedic procedures), modify the perception of pain (pharmacological and non-pharmacological), interruption of painful pathways (anesthetic blocks, chemical or physical neuroablation, spinal analgesia and surgical techniques) as well as psychological intervention. The WHO analgesic ladder constitutes a non-rigid model for the treatment of pain due to cancer, constituted by 3 steps, its dynamism presupposes an active and individualized movement starting from step 1 for the treatment of mild pain (non-opioid analgesics such as paracetamol or NSAIDs), step 2 for the treatment of mild to moderate pain (weak opioids such as codeine or dextropropoxyphene) and step 3 for the treatment of moderate to severe pain (strong opioids such as morphine). The recommended route of administration is oral and by the clock. However, adjuvant drugs such as antidepressants and anticonvulsants are included in all levels, a strategy that responds to the knowledge that 20% of cancer pain responds to primarily neuropathic mechanisms and that in more than 40% the pain is of mixed type, which includes them. Another strategy for the treatment of pain with a neuropathic component is neuroprotection that focuses on glutamatergic dysfunction, nitro-oxidative stress, mitochondrial dysfunction, apoptosis, trophic factors, neuroinflammation and undamaged fiber changes induced by neurodegeneration (Bennett, N I 2012. In: Tracey, I. editor, *IASP Refresher Courses on Pain Management*, Seattle: IASP Press, 301-304, Urch, C E and Dickenson, A H 2008. *Eur. J. Cancer* 44: 1091-1096 Bennett, M I et al., 2012. *Pain* 153: 359-365; Bordet, T. and Pruss, R M 2009. *Neurotherapeutics* 6: 648-662). It has been reported in a study of 3030 patients with cancer pain that 26% were treated with NSAIDs and 23% with paracetamol. The opioids used for the treatment of mild to moderate pain were codeine (8%), tramadol (8%), dextropropoxyphene (5%) and dihydrocodeine (2%). For moderate to severe pain, morphine was the most commonly used, 40% orally and 10% parenterally, followed by patches of fentanyl (14%), oxycodone (4%), methadone (2%) and hydromorphone (1%). The major survival of cancer patients due to immunotherapy, allows cancer to be approached as a chronic no transmissible disease, so long-term treatment with opioids and recent changes in practice such as the introduction of titration-to-effect for opioids have resulted in higher doses used in the clinic setting than ever seen previously. Consequently, in addition to its recognized adverse effects of acute installation, other emergent ones have been observed such as the development of tolerance to its analgesic effects that is inevitably associated with the successive escalation of doses, dependence and addiction, as well as hypogonadism, osteoporosis, immunosuppression, cognitive impairment and opioid-induced hyperalgesia (OIH). Combinations of low-dose opioids and adjuvants make it possible to minimize the adverse effects and titrate the doses slowly, a possibility not offered by monotherapies (Klepstad, P. et al., 2005. *Palliat, Med.* 19: 477-84, Sullivan, M D and Howe, C O 2013. *Pain* 154: S94-S100; Rivat, C. and Ballantyne, J. 2016. *Pain Reports* 1: e570). Studies in bone metastasis and primary oral cancer models showed that the pain is generated by changes in the tumor microenvironment through the secretion of mediators by the tumor cells and by the cells of the immune system (lymphocytes, macrophages, mast cells and fibroblasts) that are attracted to the tumor by mediators released by the tumor cells. These include nerve growth factor (NGF), endothelin 1, adenosine triphosphate (ATP), prostaglandin E2 (PGE2), protons H$^+$, bradykinin (BK), proteases, which activate and can sensitize nociceptors. Particularly the signaling NGF-receptor tyrosine kinase A (TrkA) expressed in sensorial neurons, is vital in the sensitization as well as inducing the phosphorylation of the channels of transient receptor potential vanilloid 1 (TRPV1), its retrograde transport to the neuronal soma induces the increase in the expression and synthesis of excitatory neuropeptides such as substance P and the peptide related to the calcitonin gene (SP and CGRP), of BK receptors, channels such as purinergic receptors (P2X), acid sensitive channels 3 (ASIC3), TRPV1, transcriptional factors such as transcription factor 3 (ATF3) associated with neural injury and structural molecules. In addition, this signaling modulates the traffic and the insertion of the sodium channels (Nav 1.8) and TRPV1 in the sensory membranes and the expression profile of Schwann cells and macrophages. Particularly, the P2X4 receptor is involved in spinal microglia-neuron signaling and the induction of mechanical hypersensitivity after peripheral neural injury. These models have also demonstrated central nervous system (CNS) changes, such as an increased expression of the NR2B subunit of N-methyl-D-aspartate (NMDA) receptors and the release of pro-inflammatory cytokines by glial cells that facilitate their phosphorylation, as well as phenotypic changes in the neuronal populations of the superficial layers of the spinal dorsal horn in murine models of breast cancer. These changes are associated with the hyperexcitability of neurons of wide dynamic range before mechanical, thermal and electrical stimuli that suggest the state of central sensitization. Glial activation and neuron-glia interactions contribute to the generation and maintenance of this process, which is not only limited to the spinal cord, but also affects brain stem areas involved in the descending modulation that facilitates pain. Consequently, tumor growth not only activates, sensitizes damages and induces regenerating sprouts in primary and sympathetic afferent neurons, also induces a significant pro-nociceptive reorganization in the CNS (Peters, C M et al., 2005. *Exp. Neurol.* 193: 85-100; Gordon-Williams, R M and Dickenson, A H 2007. *Curr. Opi. Support, Palliat. Care* 2007.1: 6-10; Yanagisawa, Y. et al., 2010. *Mol. Pain* 6:38; Latremoliere, A. and Woolf, C J 2009. *J. Pain* 10: 895-926; De Leo, J A et al., 2006. *Pain* 122: 17-21; Tsuda, M. et al., 2003. *Nature* 424: 778-83). Subsequently, drugs that alter the supraspinal bioavailability of serotonin (5-HT) and noradrenaline (NA) such as tricyclic antidepressants (TCA) and balanced inhibitors of amine reuptake, through which they increase the descending bulbospinal inhibitory modulation, show their effectiveness in the treatment of cancer pain. The favorable results achieved with the use of combinations of drugs in the WHO analgesic ladder and with bimodal or polymodal drugs such as tramadol, tapentadol, methadone, duloxetine, venlafaxine etc. that combine monomodal mechanisms interactively in a simple drug, evidence the clinical expression of the multifactorial basic dilemma of cancer pain. In addition, combination drug therapy constitutes a tendency to try to confront the phenomena of tolerance and OIH, given the convergence of the mechanisms of glutamatergic dysfunction/neuroimmune activation in the chronic pain and OIH paradigms. (Bennett, M I 2011. *Palliat, Med.* 25: 553-9; Fishbain, D. 2000, *Ann. Med.* 32: 305-16; Klepstad, P. et al., 2005. *Palliat, Med.* 19: 477-84; Mayer, D J et al., 1999. *Proc. Natl. Acad. Sci. USA* 96: 7731-7736; Tawfik, V L and De Leo, J. 2007. In DeLeo, J A, Sorkin, L S, Watkins, L R editors and glial regulation of pain Seattle: IASP Press, pp. 341-359). On the other hand, many patients affected by cancer are older than 60 years, so the inherent benefits of reducing dosage-reducing adverse effects and increasing efficacy by synergistic mechanisms and/or additive combinations of drugs, offer a greater efficacy-safety balance in the pharmacological treatment (Atkinson, T J et al., 2013. *Clin. Ther.* 35: 1669-1689; Finnerup, N B et al., 2015. *Lancet Neurol.* 14: 162-73). The formal demonstration of the synergy, as well as the proportion of each drug in the combination, requires an intensive isobologram analysis associated with pharmacological safety tests that evaluate the possible adverse effects expected for the combination of these known agents that could overlap. An interesting option for this strategy in clinical practice has been the introduction of fixed-ratio analgesic drug combination. These produce a well-standardized and reproducible clinical effect of two drugs of different classes in a formulation that can facilitate prescription and adherence to treatment by reducing the amount of medication patients should consume (Gilron, I. et al., 2013. *Lancet Neurol* 12: 1084-1095; Raffa, R B et al., 2010. *J. Pain* 11: 701-709). Particularly paracetamol, an aniline derivative is attractive for the design of combinations, because, although its precise mechanism of action has not yet been fully elucidated, it exerts its analgesic actions through multiple central mechanisms such as the inhibition of the synthesis of prostaglandins, supraspinal activation of descending inhibitory serotonergic pathways, inhibition of SP-mediated nitric oxide (NO) pathway and activation of NMDA receptors. Recently, the interaction of its metabolites with the endogenous cannabinoid system and its cannabinoid receptors 1 and 2 (CB1 and CB2) of recognized importance in the control of nociceptive transmission and chronic pain, as well as in the adaptive changes of the opioid receptors in these conditions. In addition, the weak peripheral actions of paracetamol on the synthesis of prostaglandins make it a better tolerated product than NSAIDs in terms of their impact on the gastrointestinal tract and platelet activity. However, other peripheral mechanisms through CB1 and CB2 receptors can supra-additively facilitate their effects in the affected site, locally administered through the use of topical formulations. In general, a multi-target ability of paracetamol explains its recognized analgesic efficacy (Mitchell, D. et al., 2010. *Eur. J. Pharmacol.* 642: 86-92; Bjiirkman, R. et al., 1994. *Pain* 57:259-264; Hama, H T and Sagen, J. 2010. *Neuropharmacology* 58: 758-66; Dani, M. et al., 2007. *Eur. J. Pharmacol.* 573: 214-5). On the other hand, amitriptyline, a dual inhibitor of the reuptake of 5-HT and NA, has demonstrated its efficacy in the treatment of neuropathic pain precisely because of its plurality of mechanisms inherent to the TCA class, not only because of the increase in bioavailability of amines in the synaptic cleft, but by the activation of their receptors, activation of opioid receptors (supraspinal 5 and spinal p), blocking of Na$^+$ channels, activation of K$^+$ channels, inhibition of NMDA receptor activity, facilitation of the function of GABA$_B$ receptors. As well as by other mechanisms better elucidated in this particular drug in relation to inflammatory and immune parameters of interest in cancer pain, as the reduction of the expression of the inducible nitric oxide synthase enzyme, the production of NO and tumor necrosis factor alpha (TNFα). In addition, amitriptyline peripherally modulates P2X purinergic receptors, recognized for their role in the inflammatory changes induced in the tumor microenvironment and in Wallerian degeneration. Some neurotrophic factors such as the glial cell derivative (GDNF) and the brain derivative (BDNF)

have been implicated in the actions of this drug. Likewise, its participation in the suppression of neuroinflammation and the disruption of glutamate transporters in morphine-tolerant rats has been recognized. Its local peripheral antinociceptive action has been related, at least in part, to the increase in the local bioavailability of adenosine and the activation of its A1 receptor, considered responsible for its analgesic effect. Consequently, formulations of amitriptyline in the form of gel or creams have been recommended for the treatment of inflammatory pain (Micó, J A et al., 2006. *Trends Pharmacol, Sci* 27: 348-54, Arsenault, A. and Sawynok, J. 2009. *Pain* 146: 308-314; Tai, Y H et al., 2006. *Pain* 124: 77-86; Yaron, I. et al., 1999. *Arthritis Rheum*, 42: 2561-2568, Oliveira Lima, F. et al., 2010. *Pain* 151:506-515; Sawynok, J. et al., 1999. *Pain* 80: 45-55). In WO 2005/077168 A1 a method was described for the treatment of chronic pain such as neuropathic pain and painful fibromuscular disorders, as well as compositions such as oral suspensions, tablets or capsules, containing a low dose to provide 25 mg/day or less of TCA combined with non-narcotic analgesics such as paracetamol in the range of 0.50 to 2 g/day. While TCAs as a class have definite characteristics, there are clear differences between individual agents in terms of their relative affinity for particular mechanisms, their differential contribution to clinical use and the profile of side effects (Sawynok, J. and Reid, A. 2001 *Pain* 93: 51-59).

BRIEF DESCRIPTION OF THE INVENTION

In our proposal, we selected amitriptyline for its plurality of mechanisms of interest in mixed cancer pain, which is supported by being the agent of the antidepressant group most used in patients with cancer pain with a neuropathic component (Berger et al. 2006. *Eur. J. Cancer Care* 15: 138-45). In this patent, the indication of compositions for specifically neuropathic chronic pain and painful fibromuscular disorders is protected. Neuropathic pain is conceptualized as that which is a direct consequence of injury or illness that affects the somatosensory system. This definition excludes the term of nervous system dysfunction that formerly included the concept, since it can erroneously be interpreted as plasticity changes inherent to the nociceptive system resulting from a powerful and sustained nociceptive stimulation (Treede, R D et al., 2008. *Neurology* 70:1630-1635). The term fibromuscular pain disorders should refer to fibromyalgia in the aforementioned document, one of the most frequent somatic syndromes of functional pain, related to the central amplification of the processing of sensory, cognitive and affective information, dysfunction of the endogenous nociceptive inhibitory system, disorders of sleep and dysautonomia (Clauw, D J and Williams, D A 2009. In: Mayer, E A and Bushnell, MC ed: *Functional Pain Syndromes: Presentation and pathophysiology*, Seattle: IASP Press, pp. 3-22). This patent does not describe chronic mixed pain due to cancer that is clearly distinguishable from other types of pain according to its pathophysiology and which is considered a unique form of pathological pain where inflammatory, neuropathic, ischemic components and changes in the plasticity of the nervous system converge (Harano, H. et al., 2010. *J. dent. Res.* 89: 615-20). The examples do not describe clinical efficacy trials of the proposed pharmacotherapeutic combinations with respect to the independent drugs. These are limited to 3 reports of cases with diffuse pain due to fibromyalgia, diffuse pain associated with headache and a case with pain due to osteoarthrosis of the small joints of the extremities treated specifically with doxepin and aspirin, none of these classified as neuropathic pain. A specific composition of paracetamol:amitriptyline is also not described with the advantages offered as a fixed-ratio drug combination determined by the isobolographic method that demonstrates its synergy, proportions and safety for its extrapolation of doses to humans. In our proposal we have surprisingly discovered that the fixed-ratio combination of paracetamol: amitriptyline in ranges of 11.25 to 67.5 mg/day of amitriptyline and 114 to 684 mg/day of paracetamol, produces an unexpected reduction in allodynia and mechanical hypernociception in conditions of neural injury. Also, this combination to the proportions of fixed doses determined in ranges of 1.54 to 9.24 mg/day of amitriptyline and of 76 to 453 mg/day of paracetamol produces an unexpected reduction of the persistent inflammatory pain, which allows its employment in the prevention and/or treatment of mixed pain due to cancer. Pharmacological safety and interaction studies determined that the composition shows an increment in efficacy by synergistic mechanisms, reduced dosage and adverse effects, so it can offer greater efficacy-safety balance in this type of patient, particularly for paracetamol known by its hepatic and renal toxicities, which in the composition is reduced by more than ¼ of its usual daily dose.

An object of the present invention is a pharmaceutical composition at a fixed dose, which comprises paracetamol, a non-narcotic analgesic and amitriptyline, a tricyclic antidepressant with anti-inflammatory and immunomodulatory mechanisms, as well as at least one pharmaceutically acceptable excipient.

Another object of the present invention relates to providing the proportions of the drugs to be combined and the effective doses of the combinations studied for their more efficient and safe extrapolation to humans. Those that result from the isobolographic study and pharmacological safety in two animal models, one of persistent pain where the changes of acute plasticity of the CNS lie and another neuropathic, whose main pathophysiological mechanism is neuroinflammation.

It is also an object of the present invention to provide the development of pharmaceutical compositions with advantages compared to pharmaceutical formulations in the prior state of art. In particular, this composition, being a fixed-ratio drug combination, facilitates the prescription and adherence to treatment, shows an increase in efficacy by synergistic mechanisms, in particular for the reduction of mechanical allodynia, mechanical hypernociception and persistent inflammatory pain, reduction of the dosage of both drugs and adverse effects, so it can offer a greater efficacy-safety balance.

Another object of the present invention is a method for the treatment of mixed pain due to mild cancer usually treated with drugs of the step 1 of the WHO analgesic ladder, in which the composition provided in this invention is administered. This can also be administered for the treatment of mild to moderate pain associated with weak opioids used in step 2 or moderate to severe associated with powerful opioids used in step 3, to improve its analgesic efficacy.

Yet another aspect of the present invention is the use of the combination to protect from degeneration induced by neuroinflammation after neural injury (preventive and/or therapeutic effect), which may occur by infiltration or tumor compression of the sensory fibers or their therapeutic in mixed pain due to cancer where inflammatory, neuropathic and ischemic mechanisms converge to generate pain.

In a preferred embodiment, the amitriptyline is present in an amount between 1-22.5 mg, and the paracetamol is present in an amount between 49-227.5 mg. In another preferred embodiment, the composition is in the form of a tablet, nasal spray, powder for inhalation, ointment, patch, solution or suspension for infusion. Preferably, the pharmaceutical combination is administered one or more times per day.

BRIEF DESCRIPTION OF THE DRAWINGS

FIG. 3 Antihypernociceptive effect of increasing doses of amitriptyline (A) and paracetamol (B) on the behavior of licking/biting during phase II of the 2.5% formalin test in rats, expressed as a percentage of antinociception or maximum possible effect.

FIG. 4 Antihypernociceptive effect of increasing doses of the combination paracetamol:amitriptyline on the behavior of licking/biting during phase II of the 2.5% formalin test in rats, expressed as a percentage of antinociception or maximum possible effect.

FIG. 9 Antiallodynic effect (A) and mechanical antihypernociceptive (B) of increasing doses of paracetamol expressed as a percentage of the maximum possible effect (% MPE) compared to gabapentin or vehicle in the ipsilateral hindpaw of CCI rats.

FIG. 10 Effect of increasing doses of the paracetamol: amitriptyline combination (C1-C4), compared with gabapentin or vehicle on mechanical allodynia (A) and mechanical hypernociception (B) in the ipsilateral hindpaw of CCI rats.

FIG. 11 Antiallodynic (A) and mechanical antihypernociceptive (B) effect of increasing doses of the paracetamol: amitriptyline combination (C1-C4) expressed as a percentage of the maximum possible effect (% MPE) compared to gabapentin or vehicle in CCI rats.

FIG. 12 Isobolographic analysis showing the synergistic antiallodynic interaction of the oral combination paracetamol:amitriptyline at repeated doses after 7 days of induction of damage by chronic constriction of the sciatic nerve in rats.

DETAILED DESCRIPTION OF THE INVENTION

Figure 1:
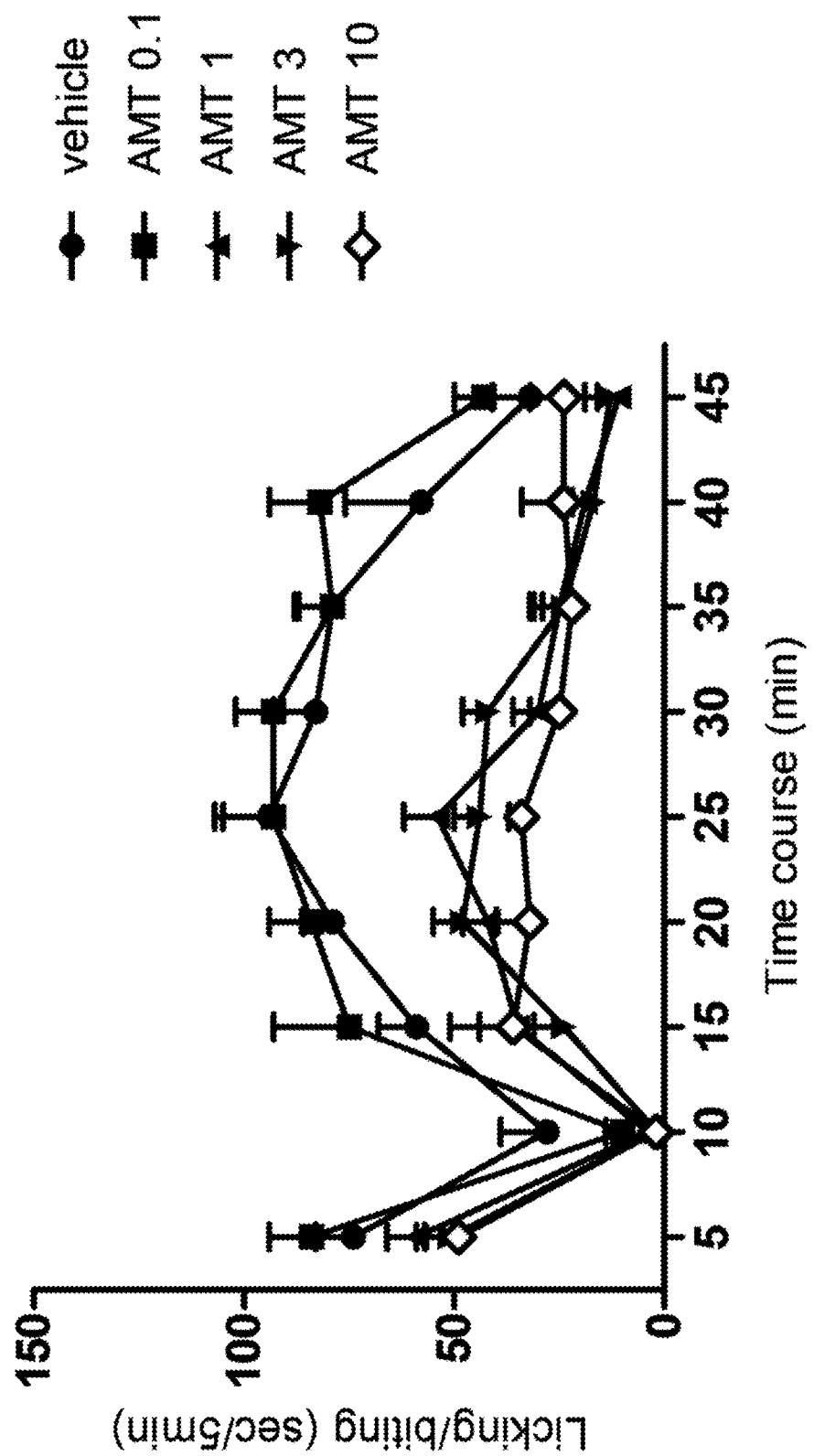
FIG. 1 Temporal course of the effect of increasing doses of amitriptyline with respect to vehicle on the behavior of licking/biting after injection of 2.5% formalin in the plantar surface of the rat's paw.
Figure 2:
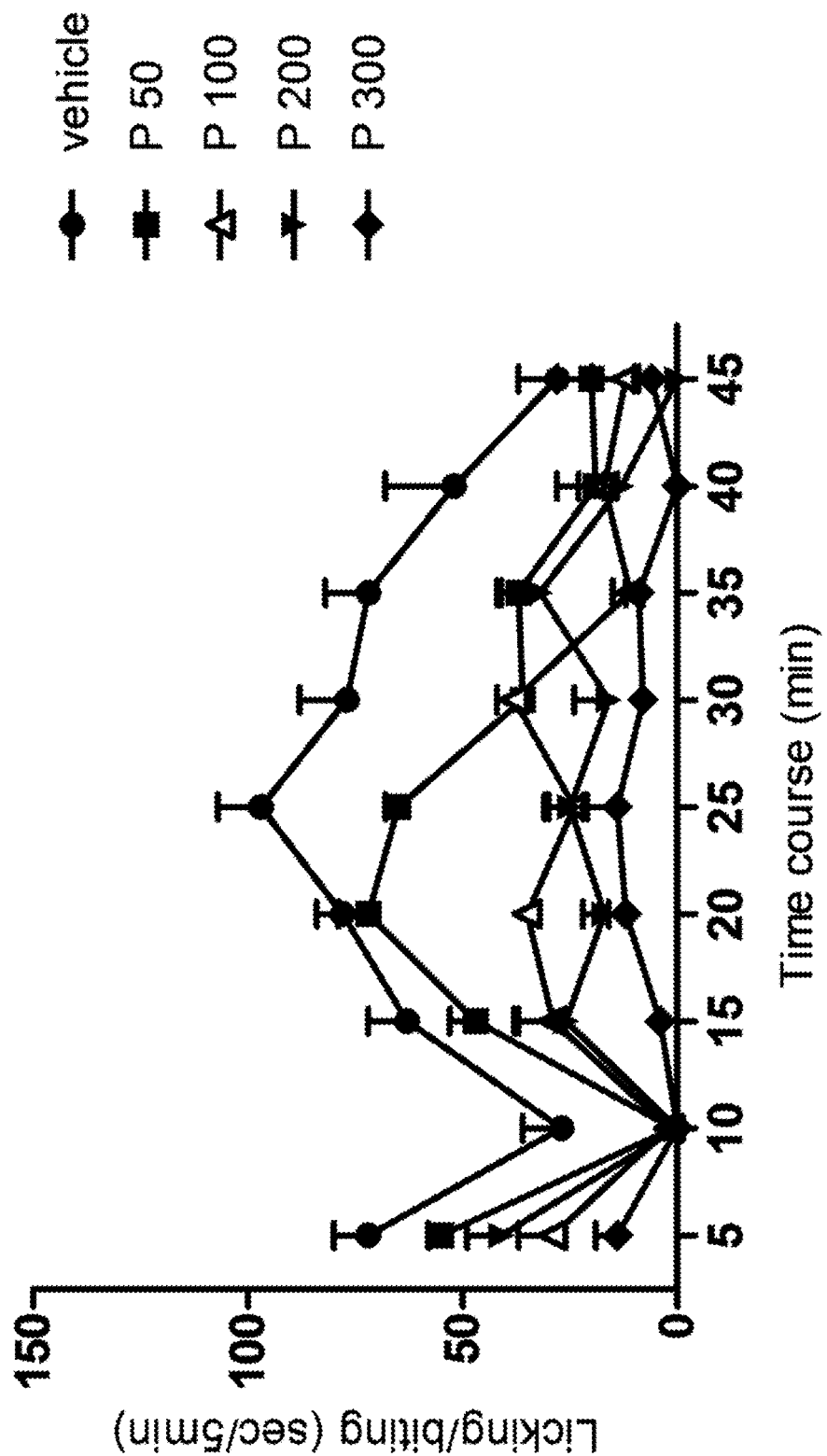
FIG. 2 Temporal course of the effect of increasing doses of paracetamol with respect to vehicle on the behavior of licking/biting after injection of 2.5% formalin on the plantar surface of the rat's paw.
Figure 5:
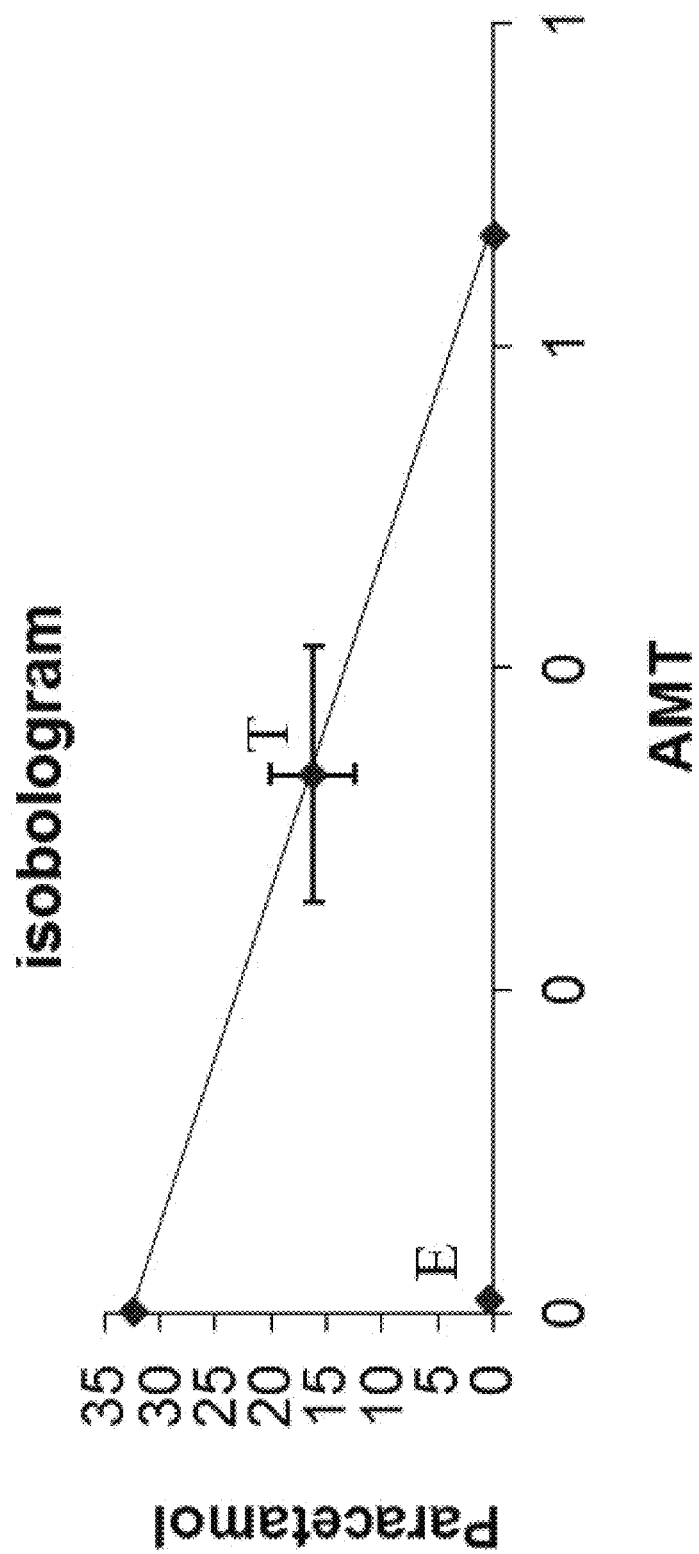
FIG. 5 Isobolographic analysis showing the synergistic antihypernociceptive interaction of the oral combination paracetamol:amitriptyline at a single dose during phase II of the 2.5% formalin test in rats.

In the present invention referred to the combination paracetamol:amitriptyline, the pharmacodynamic rationality was based on the knowledge of the actions of both drugs on the nociceptive pathways considering the multiple sites and mechanisms operating on specific targets, as well as their adverse effects and pharmacokinetic variables. The pharmacological interaction study of both drugs was designed for the formal demonstration of synergy by means of an intensive isobolographic analysis (analysis of graphs plotting different doses of the two drugs to produce constant efficacy along and in combination) in two models in vivo. This responds to the need for the use of integral systems in which peripheral activity, spinal transmission, modulating systems and suprasegmental systems of the active global network that leads to the perception of pain can interact (Raffa, R B et al., 2010. *J Pain* 11: 701-709). The experiments were designed in young rats (8-10 weeks, Sprague Dawley, males, 168-240 g, CENPALAB, Havana, Cuba) and divided into several groups n=6-7 each, which received increasing doses of both drugs independent and combinations, to evaluate the effect as a percentage (%) of antinociception at single doses in the formalin test compared to the vehicle-treated group. This test is considered a standard persistent pain model for the study of animal nociception, widely used (Okuda, K. et al., 2001. *Pain* 92: 107-15). A biphasic nociceptive behavior has been described in this test, the first phase or nociceptive is interpreted as a consequence of the direct activation of the peripheral endings of the nociceptors by the chemical irritant. While the second, tonic or late phase is interpreted as the result of the acute inflammatory response, as well as the peripheral and central sensitization produced by the sustained activation of C fibers (Coderre, T J et al., 1990. *Brain Res.* 535: 155-8). This phase mimics the changes in synaptic plasticity that occur during persistent pain that could progress to chronicity, which is why it received the greatest attention in our experiments. The period between the two phases of the response is identified as a phase of latency in which the activity diminishes or practically ceases, this effect being attributed to the participation of the mechanisms of central endogenous pain modulation (Dubuisson, D. and, Dennis, S G 1977. *Pain* 4: 161-74; Omote, K. et al., 1998. *Brain Res.* 814: 194-8). The time course of the antinociceptive response to individual drugs and combinations was constructed by mapping the mean time of the licking/biting as a function of the time of each phase. These values were transformed into percentage of antinociception that express the percentage of inhibition of the behavior with respect to the control of the particular phase according to the formula: % antinociception=$((x-x1)/x)*100$. Where X=average time of licking/bite of the control group treated with vehicle, X1=time of licking/biting of each animal of the experimental group (for phase I licking time in 5 minutes, for phase II average of the time of 15 to 45 minutes per animal). In the case that X1 was greater than X, a value of 0 was assigned to % antinociception. A value close to 0% means that the behavior is similar to that of the control group and a value close to 100% means that there was no nocidefensive behavior (Argelles, C. F. et al., 2002. *Anesthesiology* 96: 921-5). The antihyperalgesic effect of amitriptyline has been recognized in neural damage conditions. However, in this test the drug shows differential actions on nocidefensive behaviors at the spinal and supraspinal levels (Densmore, V S et al., 2010. *Pain* 151: 184-193 Sawynok, J. and Reid, A. 2001. *Pain* 93: 51-59). One of the proposals to explain these discrepancies has been the ability of amitriptyline to increase serotonergic signaling, which has multiple subtypes of receptors, some low and others with high affinity, with heterogeneous and even opposite actions distributed at different levels of the nociceptive pathways. The 5-HT1A, 5-HT1B, 5-HT1D receptors possess inhibitory actions on nociceptive transmission through direct mechanisms by pre-synaptic and post-synaptic inhibition in superficial layers of the spinal dorsal horn. However, 5-HT2A and 5-HT3, 5-HT4 and 5-HT7 localized pre-synaptically facilitate it. It has been suggested that the interaction of this drug with high affinity receptors of 5-HT can explain its analgesic efficacy at low doses and the phenomenon of hormesis that shows its dose-response curve (Suzuki, R. et al., 2004. *Trends Pharmacol. Sci.* 25: 613-7). At doses of 20, 25, 50 and 100 mg/kg, a significant dose-dependent inhibitory response pattern was not observed on the licking/biting response in both phases and withdrawal responses that are mainly spinally processed were increased. As a consequence, the most integrated licking/biting behavior was recorded and doses of amitriptyline (0.1, 1, 3, 10 mg/kg, p.o., AMT) were used for the dose-response curve study (FIG. 1). A significant inhibitory effect was observed exclusively on phase II at the doses used and the effective dose 30 (ED30) for the inhibition of nociceptive behavior during this phase was ED30=0.6677. The percentages of inhibition of phase II (−11.38485681, 57.3479796, 55.55904276, 62.24401726 respectively for the doses of 0.1, 1, 3, 10 mg/kg) were statistically significant from the dose 1 mg/kg (p<0.001) (FIG. 3A). For the study of the dose-response curve of paracetamol, increasing doses were used (50, 100, 200, 300 mg/kg, po, P) according to previous reports in more studied models of inflammation and its recent introduction in a neuropathic pain model (Lee, Y S et al., 2007. *Pain* 129: 279-286; Im, K S et al., 2012. *Kaohsiung Journal of Medical Sciences* 28: 251-258). Despite its weak inhibitory activity of cyclooxygenase enzymes, this drug reduces the release of spinal prostaglandin E2 in the formalin test. After oral administration of paracetamol or acetaminophen, it is deacetylated in the liver to p-aminophenol and metabolized to AM404 in the brain by the amide hydrolase of fatty acids (FAAH), this metabolite reinforces the activity of the supraspinal cannabinoid system by inhibiting the reuptake and degradation of its endogenous anandamide ligand, which, through the CB1 receptors, reinforces the activity of the serotonergic downstream pathways. The release of 5-HT spinal stimulates 5-HT receptors by inhibiting nociceptive transmission mainly of chemical stimuli such as formalin (5-HT1A) and mechanical (5-HT3/4). Lipoamino acid AM404 is an agonist of TRPV1 receptors in the brain and can also facilitate the inhibition of T-type voltage-gated calcium channels widely distributed in cortical and subcortical areas involved in pain modulation (Mallet, C. et al. 2008. *Pain* 139: 190-200; Kerckhove, N. et al, 2014. *Pain* 155: 764-772; Bonnefont, J. et al., 2005. *Pain* 114: 482-490). Although a classic inhibitory effect of the dose-dependent nociceptive behavior of paracetamol was observed on both phases of the test, exclusively the dose higher than 300 mg/kg significantly reduced phase I, while all the doses used significantly reduced phase II (FIG. 2, FIG. 3B). The ED30 for the inhibition of phase II was ED30=32.3578. The percentages of inhibition of phase II (38.075018, 65.734843, 74.239207, 87.780137 respectively for doses 50, 100, 200 and 300 mg/kg) were statistically significant (p<0.001) (FIG. 3B). The results obtained with each independent drug allowed access to the theoretical data to calculate the experimental fractions of the combination and to design the dose-response curve study in the formalin test and isobologram. It was decided to work with ED30 although in both cases we obtained responses superior to 50% of % antinociception, for safety reasons in relation to the adverse effects associated with both drugs, since the design in function of ED50 also presupposes higher doses for the study of the combination that would be used in the long term in a majority population of the third age. This special population presents a greater risk of overdose, toxicities and drug-drug and drug-disease interactions, due to the pharmacokinetic changes associated with aging and the comorbidities that lead to polypharmacy (Harvey, W F and Hunter, D J 2010. *Clin. Geriatr. Med* 26: 503-515). Particularly, amitriptyline is not recommended at doses higher than 75 mg/day in adults over 65 years of age due to more intense anticholinergic and sedative adverse effects with risk of falls, cognitive dysfunction, constipation, urinary retention, dry mouth, cardiovascular effects, orthostatic hypotension). Doses greater than 100 mg/day have been associated with an increased risk of sudden cardiac death (Finnerup, N. B. et al., 2015. *Lancet Neurol.*, 14: 162-73). Based on the calculation of the ED30 theoretical=16.51277582 of the combination in proportions of 0.5 of each drug, the doses of the combination were calculated from the fractions of the theoretical proportion of ED30 that constitutes the maximum dose (2, 4, 8, 16 mg/Kg, po, C1, C2, C3, C4). A % of antinociception was observed by exclusively inhibiting dose-dependent phase II with values of 44.3913203 for the dose 2 mg/kg (p<0.01) and 53.0414594, 57.0062523, 64.1632953% from of the dose 4 mg/kg respectively (p<0.001) (FIG. 4). The experimental ED30=0.3923 and the experimental point is located below the line of additivity in correspondence with a synergistic interaction (FIG. 5). For an interaction index (ED30experimental/ED30theoretical) of 0.02375799, less than 1 statistically significant (Table 2). No signs of general and CNS toxicity were observed. The reduction of the doses of both drugs in the combination constitutes a favorable element in the safety paradigm, considering the adverse effects of the tricyclic antidepressants for their actions on several neurotransmission systems that are more evident when scaling their doses, as well as the hepatic and renal toxicities described for paracetamol.

TABLE 1

Dosage (mg/kg) used in the interaction study of amitriptyline and paracetamol after oral administration in the formalin test.

| Amitriptyline in the combination | Paracetamol In the combination | Total dose |
| --- | --- | --- |
| 0.04 | 1.96 | 2.0 |
| 0.08 | 3.92 | 4.1 |
| 0.16 | 7.84 | 8.2 |
| 0.32 | 15.68 | 16.5 |

TABLE 2

Effective doses calculated after oral administration of amitriptyline and paracetamol independent or combined in the formalin test.

| | Oral administration ED30 (mg/kg) |
| --- | --- |
| Amitriptyline | 0.66 ± 0.41 |
| Paracetamol | 32.35 ± 7.85 |
| Theoretical combination | 16.51 ± 3.93 |

TABLE 2-continued

Effective doses calculated after oral administration of amitriptyline and paracetamol independent or combined in the formalin test.

| | Oral administration ED30 (mg/kg) |
|---|---|
| Experimental combination | 0.39 ± 0.10* |
| Interaction index | 0.023 |

Figure 6A:
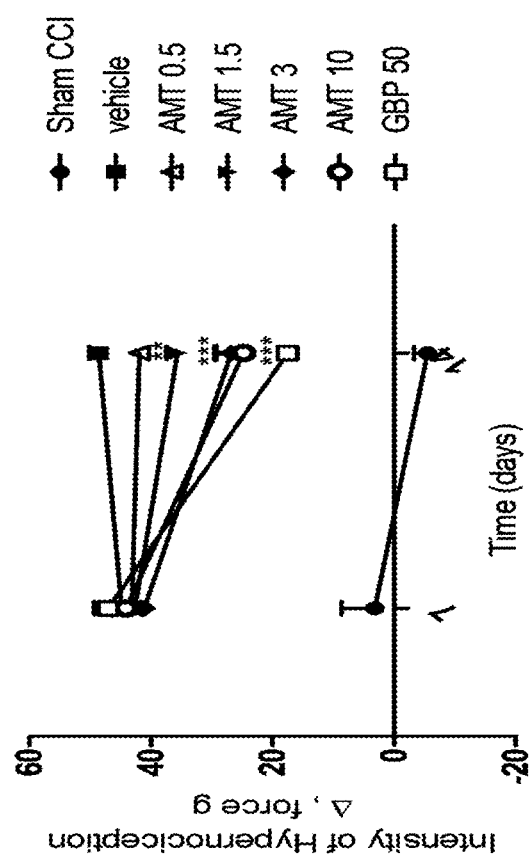
FIG. 6 Effect of increasing doses of amitriptyline compared to gabapentin or vehicle on mechanical allodynia (A) and mechanical hypernociception (B) in the ipsilateral hindpaw of CCI rats.
Figure 6B:
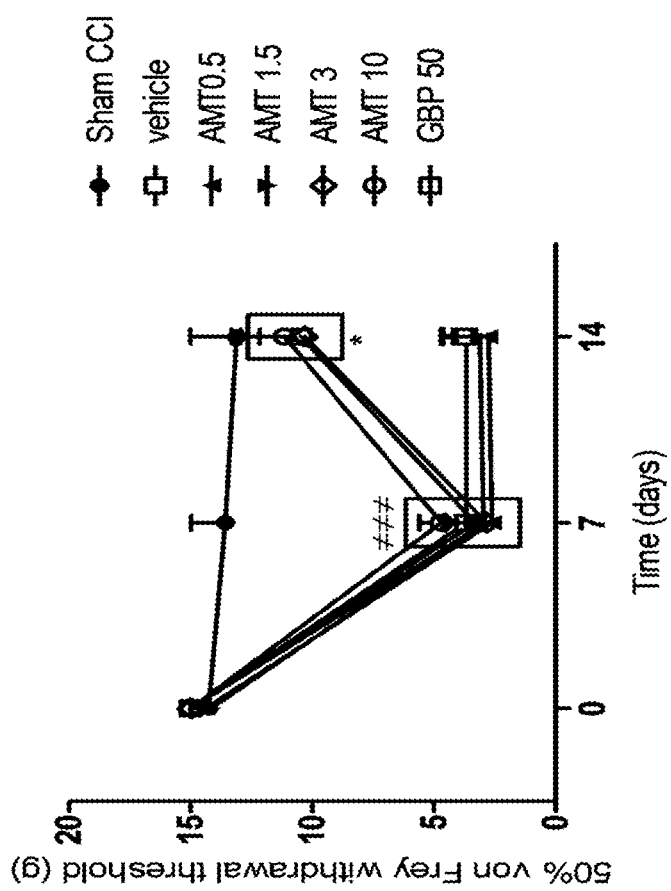
Figure 7B:
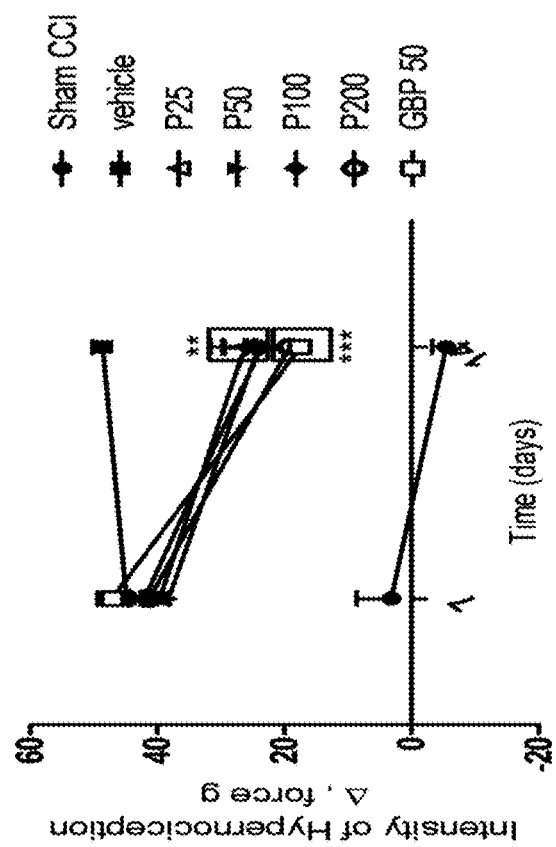
FIG. 7 Effect of increasing doses of paracetamol compared to gabapentin or vehicle on mechanical allodynia (A) and mechanical hypernociception (B) in the ipsilateral hindpaw of CCI rats FIG. 8 Antiallodynic effect (A) and mechanical antihypernociceptive (B) of increasing doses of amitriptyline expressed as a percentage of the maximum possible effect (% MPE) compared to gabapentin or vehicle in the ipsilateral hindpaw of CCI rats.
Figure 7A:
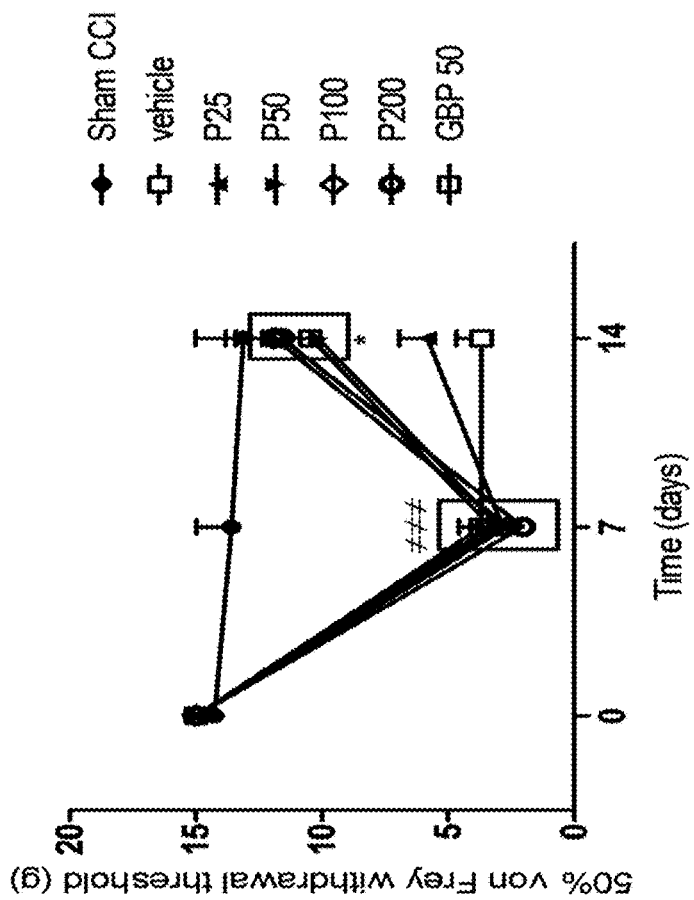
Figure 8B:
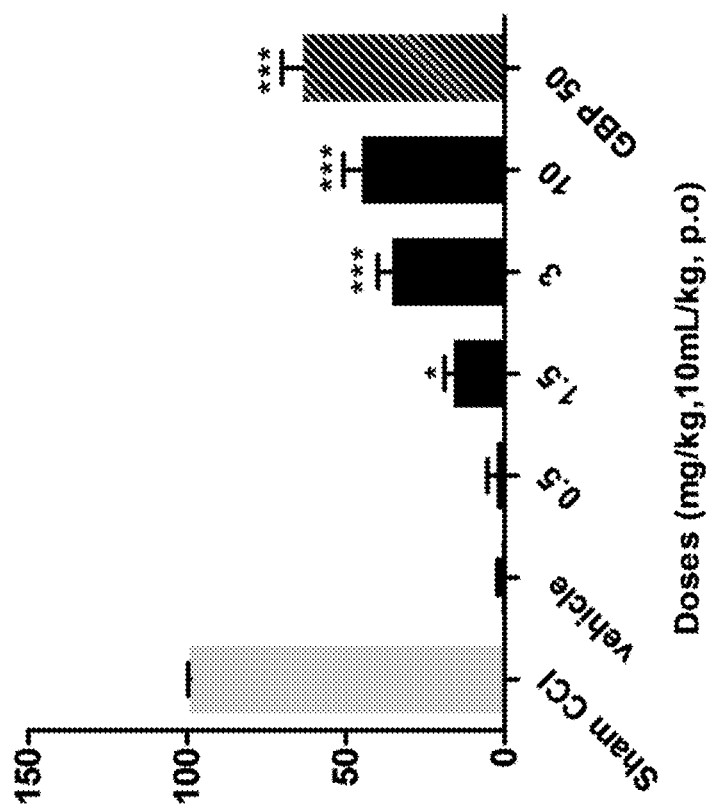
Figure 8A:
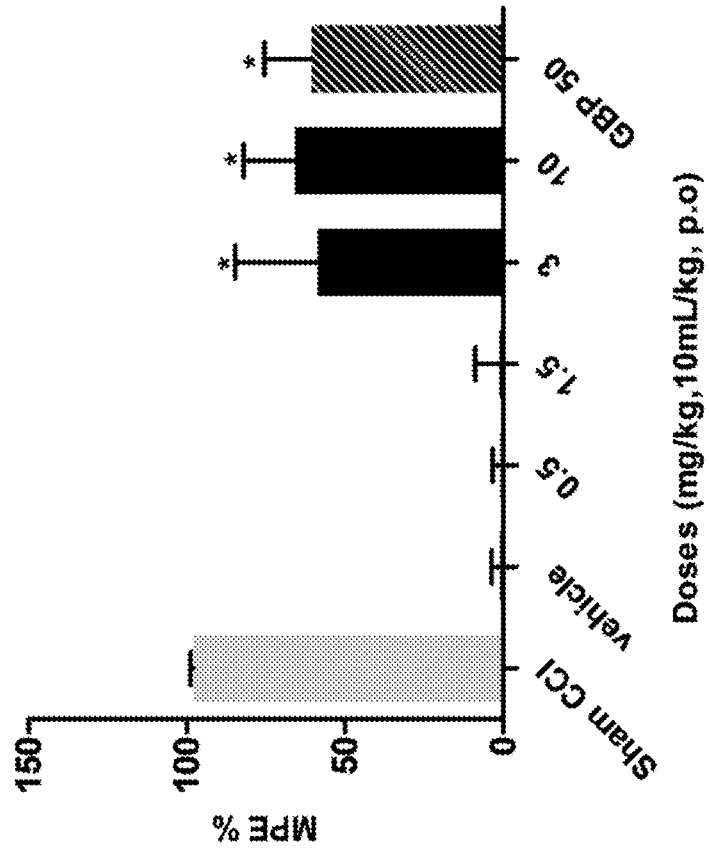

ED30: effective dose that produces 30% reduction on the control response.
The data is the mean ± SD of the estimate. *Significant differences with respect to the data of the theoretical combination ($p < 0.05$), by Student's test The favorable results at a single dose in phase II of this algesymmetric test provide evidence that allows us to move towards a neuropathic pain model to study the possible combination at repeated doses. Correspondingly, another design was executed in the sciatic nerve chronic constriction model (CCI), a neuropathic pain model whose main pathophysiological mechanism is neuroinflammation associated with Wallerian degeneration (WD) (Bennett, G J and Xie, Y K 1988. Pain 33: 87-107; Berger, J V et al., 2011. Brain Res. Rev. 67: 282-310). The CCI model has a high sensitivity (88%) for the prediction of efficacy in controlled clinical trials (Kontinen, V K and Meert, T F 2003. In: Dostrovsky, J O, Carr, D B, Koltzenburg, M. editors. the 10th World Congress on Pain, Seattle: IASP Press, p. 489-98). Once the model was reproduced, the threshold of removal of the injured hindpaw was measured by the stimulation with the von Frey filaments (mechanical allodynia) and by the stimulation with an electronic von Frey (mechanical hypernociception). The measurements were performed under baseline conditions and at 7 days post-CCI (hyperalgesic peak in the model), at which time the experimental groups were conformed (n=6-7 per group) to proceed with the dose-response curve study of amitriptyline. In this way, establish the ED30 or ED50 depending on the % of maximum possible effect (MPE) produced by the drug to reduce each of the sensory symptoms of neuropathic pain reproduced by the model (Jensen, T S and Baron, R. 2003. Pain 102: 1-8). Gabapentin, a common drug in its treatment, was used as a reference. CCI-vehicle group (distilled water 10 mL/kg, p.o.), amitriptyline groups (0.5, 1.5, 3, 10 mg/kg, p.o., AMT), gabapentin group (50 mg/kg, p.o., GBP); Sham CCI Group (distilled water 10 mL/kg, p.o.) The daily supply was given at repeated doses for 7 days until 14 days post-CCI, at which time another evaluation of the variables was performed. Amitriptyline at doses of 3 and 10 mg/kg increased the withdrawal thresholds of the damaged paw to von Frey filaments stimulation ($p<0.05$), in addition it significantly reduced the intensity of mechanical hypernociception at a dose of 1.5 ($p<0.01$), 3 and 10 mg/kg ($p<0.001$) (FIG. 6A and FIG. 6B). The experimental groups were formed for the dose-response curve study of paracetamol: CCI-vehicle group (distilled water 10 mL/kg, p.o.), Paracetamol groups (25, 50, 100, 200 mg/kg, p.o., P), Gabapentin group (50 mg/kg, p.o., GBP), CCI Sham Group (distilled water 10 mL/kg, p.o.). These doses of paracetamol have not been associated with liver or kidney damage in rats. Paracetamol showed significant antiallodynic effect from doses of 50 mg/kg ($p<0.05$) and mechanical antihypernociceptive effect in a dose-dependent manner 25, 50, 100 ($p<0.01$) and 200 mg/kg ($p<0.001$) similar to the GBP (FIG. 7A and FIG. 7B). To execute the dose-response curve mapping, the withdrawal thresholds after the treatments were converted into % of MPE. [Mechanical allodynia: MPE %=(post-treatment threshold−pre-treatment threshold)/(15 g-pre-treatment threshold)×100; Mechanical hypernociception: MPE % (Δ g post-treatment−Δ g pre-treatment)/50−Δ g pre-treatment)×100]. Subsequently, the same design was executed with the four doses of the combination calculated from the theoretical effective dose of each drug, this was calculated for each variable depending on the ED50 or ED30 according to the drug's capacity to obtain 50% or more of MPE that is 100% assumed as the total suppression of mechanical allodynia and mechanical hypernociception induced by CCI. In the presence of mechanical allodynia, amitriptyline, according to the doses used, showed the following MPE values: 0.5 mg/kg=0.96%, 1.5 mg/kg=1.31%, 3 mg/kg=58.75% ($p<0.05$), 10 mg/kg=65.97% ($p<0.05$) vs GBP 50 mg/kg=60.66% ($p<0.05$), ED50=4.5422 (FIG. 8A). In addition, concerning to the hypernociception intensity, the MPE values: 0.5 mg/kg=2.55%, 1.5 mg/kg=16.07% ($p<0.05$), 3 mg/kg=35.43% ($p<0.001$), 10 mg/kg=44.95% ($p<0.001$) vs GBP 50 mg/kg=63.47% ($p<0.001$), ED30=3.1032 (FIG. 8B). Amitriptyline inhibited both alterations of nociceptive processing but the potency of its effect was in the following order: mechanical allodynia>mechanical hypernociception. In neuropathic pain models there are controversies regarding the observation of the mechanical antiallodynic effect of amitriptyline. Particularly in the CCI model using higher doses 32, 64 and 128 mg/kg, this drug reduced the thermal hypernociception but did not show an antiallodynic effect. The result was similar in the model of spared neural injury (SNI), instead it reversed the responses to stimuli induced by chemical irritants induced by ATP and capsaicin, stimuli that are transmitted by the C fibers that express P2X and TRPV1 receptors and that are also involved in the transmission of thermal stimuli. Mechanical allodynia after neural injury in rats, may reflect greater activity in A fibers than in C fibers, so the differential effect of amitriptyline on these two variables reflects actions of the drug on different types of fibers (De Vry, J. et al., 2004. Eur. J. Pharmacol. 491: 137-148; Arsenault, A. and Sawynok, J. 2009. Pain 146: 308-314; Benbouzid, M. et al., 2008. Eur. J. Pain 12: 1008-17). We now find that by using repeated minor doses in the CCI model, the effects on mechanical sensory alterations are observed, with no signs of sedation or catalepsy. On the other hand, paracetamol has been scarcely studied in neuropathic pain models, but it has been reported that it reduces thermal hyperalgesia, mechanical allodynia and cold allodynia in the CCI model. In the present experiment doses of 300 mg/kg showed less efficacy to reduce the intensity of mechanical hypernociception than those of 200 mg/kg, so for the design of their dose-response curve study, we decided not to use doses higher than 200 mg/kg, considering that the paracetamol also interacts with the heterogeneous family of 5-HT receptors through the cannabinoid system. Particularly, before mechanical stimuli as evaluated in present experiment, this drug could mediate its analgesic actions through excitatory 5-HT receptors located in inhibitory gabaergic interneurons such as 5-HT3 and 5-HT4 (Im, K S et al., 2012. Kaohsiung Journal of Medical Sciences 28: 251-258; Suzuki, R. et al., 2004. Trends Pharmacol. Sci. 25: 613-7). Acetaminophen regarding to mechanical allodynia showed MPE values: 25 mg/kg=25.65%, 50 mg/kg=60.96% ($p<0.05$), 100 mg/kg=75.49% ($p<0.01$), 200 mg/kg=75.45% ($p<0.01$), GBP 50 mg/kg=60.66% ($p<0.05$), ED50=47.5484 (FIG. 9A). In addition, in view of the intensity of mechanical hypernociception, the MPE values were: 25 mg/kg=31.79% ($p<0.01$), 50 mg/kg=35.05% ($p<0.01$), 100 mg/kg=42.42% ($p<0.001$), 200 mg/kg=48.37% ($p<0.001$), GBP 50 mg/kg=63.47% ($p<0.001$), ED30=22.5725 (FIG. 9B). Paracetamol inhibited both sensory alterations evoked by mechanical stimuli in this model, but its effect was also more robust above mechanical allodynia>mechanical hypernociception. The theoretical effective dosses where calculated for each variable in function of ED30 and ED50 depending on the capacity of the drug to obtain 50% of the MPE in each case. [mechanical allodynia: ED theoretical=26.04530269 (ED50); mechanical hypernociception ED theoretical=12.83786895 (ED30)]. In order to design the isobolographic analysis the experimental fractions of the combination where calculated according to ED50 starting from the archived effect over the mechanical allodynia variable (VF filaments). The calculated doses where (C1-C4: 3, 7, 13 and 26 mg/kg respectively) (Table 3). These where administrated by oral route daily starting from day 7 post-CCI at the hyperalgesic peek during 7 days until day 14 post-CCI. The combination paracetamol: amitriptyline showed mechanical antiallodynic and antihypernociceptive effects in a dose dependent form C3 ($p<0.01$), C4 ($p<0.001$) 14 days post-CCI (FIG. 10A and FIG. 10B).

TABLE 3

Antiallodynic dosage (mg/kg) used in the interaction study of amitriptyline andparacetamol after oral administration in the sciatic nerve chronic constriction model.

| Amitriptyline in the combination | Paracetamol in the combination | Total dose |
|---|---|---|
| 0.27 | 2.73 | 3 |
| 0.63 | 6.67 | 7 |
| 1.17 | 11.83 | 13 |
| 2.34 | 23.66 | 26 |

The therapeutic effect expressed as MPE % was C1=14.40%, C2=47.60%, C3=72% ($p<0.05$), C4=95% ($p<0.01$), GBP=67, 16% ($p<0.05$) (FIG. 11A). C3 and C4 were higher than the GBP 50 mg/kg in their mechanical antiallodynic effect. The experimental ED50 was 8.2178 mg/kg, while the theoretical one was 26.0453 mg/kg, so the combination showed a synergistic effect with an interaction index of 0.31, statistically significant (FIG. 12 and Table 4). Regarding the pharmacological safety tests that were associated with this experiment, it was observed that at the therapeutic doses used no motor alterations, sedation or catalepsy were observed before acute oral administration measured at 30 min, hours 1, 2 and 3 after its supply, also after the 7 successive doses. Surprisingly we observed that these doses calculated from the antiallodynic ED theoretical of the combination also significantly inhibited mechanical hypernociception, with % values of MPE for C3 and C4 higher than those reached by each independent drug, as well as similar to the GBP values (MPE %: C1=7.61%, C2=20.79%, C3=58.80% ($p<0.01$), C4=67.97% ($p<0.01$), GBP=63.47% ($p<0.01$) (FIG. 11B).

TABLE 4

Effective antiallodynic doses calculated after oral administration of amitriptyline and paracetamol independent or combined in the sciatic nerve chronic constriction model

| | Oral administration ED50 (mg/kg) |
|---|---|
| Amitriptyline | 4.54 ± 2.28 |
| Paracetamol | 47.54 ± 14.13 |
| Theoretical combination | 26.04 ± 7.16 |
| Experimental combination | 8.21 ± 0.77* |
| Interaction index | 0.31 |

ED50: effective dose that produces 50% reduction on the control response.
The data is the mean ± SD of the estimate. *Significant differences with respect to the data of the theoretical combination ($p < 0.05$), by Student's test.

Figure 13:
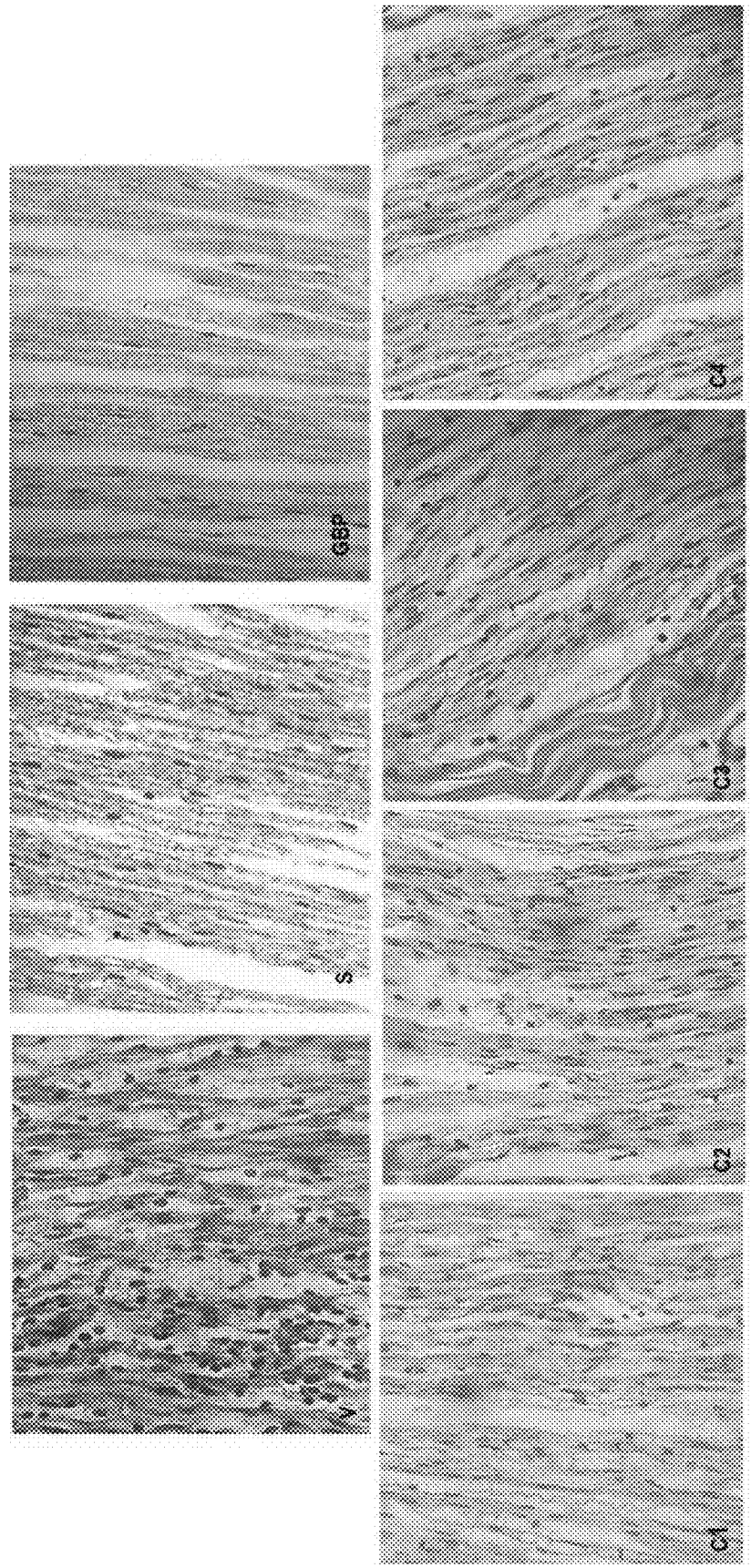
FIG. 13. Qualitative histopathological analysis of rat sciatic nerve sections to evaluate the neuroprotective effect of the paracetamol:amitriptyline combination on the chronic sciatic nerve constriction (CCI)-induced Wallerian degeneration-related changes at 14 days post-surgery.

On the other hand, we observed an unexpected reduction of the CCI-induced WD-related histopathological changes using this combination at doses 13 and 26 mg/kg (C3 and C4, respectively) such as: disorganization of the nerve fibers and the increase of the cell number (proliferation of Shawann cells and infiltration of macrophages) and the degradation of the myelin sheaths observed in the animals treated with vehicle (V) with respect to the sham operated animals (S) (FIG. 13). This result suggests a certain protective effect on the process of neuroinflammation that occurs during WD and was based on the qualitative observation of a 5 mm section distal to the lesion of the sciatic nerve of CCI rats. These animals received the combination at repeated doses for 7 days from day 7 post-CCI until day 14 after the surgery, when they were sacrificed. Although some neuroprotective actions of TCAs are recognized, the reduction of these changes for independent drugs has not been reported and could be another mechanism that explains the mechanical antiallodynic effect of the combination. This sensory alteration has been related to the axonal degeneration of Aβ fibers of the sciatic nerve and the regeneration changes associated with nerve growth factor (NGF) that occur during WD in the evaluated period of the model. Although the supply of the combination began 7 days after the induction of injury once mechanical allodynia (therapeutic effect) was established, the DW processes that start 24 hours after the damage continue for 3 or more weeks. Hence, a preventive effect in early stages on the evolution of these processes could be significant, particularly the invasion of neutrophils that occurs around 7 days contributes to the peripheral mechanisms of neuropathic pain (Ramer, M S et al, 1997. *Pain* 72: 71-8 Berger, J V et al., 2011. *Brain Res.* Rev. 67: 282-310; Debovf, P. 2011. *Annals of Anatomy* 193: 267-275). Correspondingly, the anti-inflammatory actions of amitriptyline that could be relevant in this effect have been described, such as the reduction of the release of pro-inflammatory cytokines (TNFα and IL-1β) and the peripheral modulation of P2X purinergic receptors. These are expressed in the Shawann cells that, due to the axonal disconnection, shifts to an activated phenotype, the ATP-P2X7 signaling promotes the synthesis of NGF, pro-inflammatory cytokines and chemokines during the neuroinflammatory response of the WD. CCI animals show reduced expression of GDNF and their supply can reduce mechanical allodynia relative to the undertrophed pattern of damaged fibers with a decrease in GDNF signaling that protects from phenotypic changes. While healthy fibers have an overtrophed pattern with increased NGF signaling that is pro-nociceptive.

Amitriptyline can increase the synthesis and release of some neurotrophic factors such as GDNF and BDNF that could provide neuroprotection in these conditions, as well as the reinforcement of the cannabinoid system that induces paracetamol through CB2 receptors that are expressed mainly in immune cells involved in the WD process. (Tai, Y H et al, 2006. *Pain* 124: 77-86; Arsenault, A. and Sawynok, J. 2009. *Pain* 146: 308-314; Üçeiler, N. and Sommer, C. 2006. *Drug Discovery Today: Disease Mechanism* DOI: 10.1016/j.ddmec.2006.09.004; Nagano, M. et al., 2003. *Br. J. Pharmacol.* 140: 1252-60; Griffin, J W 2006. In: Campbell, J N, Basbaum, A I, Dray, A., Dubner, R., Dworkin, R H, Sang, C N, editors, *Emerging strategies for the treatment of neuropathic pain*, Seattle: IASP Press, p 271-90, Austin, P L and Moalem-Taylor, G. 2010. *Journal of Neuroimmunology* 229: 26-50).

In a further aspect the present invention relates to a pharmaceutical dosage form comprising the pharmaceutical combination of the invention as described above and one or more auxiliary agents.

In an another aspect, the pharmaceutical dosage form of the invention is suitable to be administered orally, intranasally, topically, transdermally or intravenously.

The formulations and dosage forms of the invention may contain auxiliary agents, for example, carriers, fillers, solvents, diluents, colorants and/or binders. The selection of auxiliary agents and the amounts thereof to be used depends, for example, on how the medicament is to be administered, whether orally, intranasally, topically, transdermally or intravenously.

To obtain a solid formulation such as a tablet, for example, the components of the pharmaceutical composition include but are not limited to, Lactose monohydrate, Carboxymethyl sodium starch, Polyvinylpyrrolidone K-25, Glycerin, Magnesium stearate, Ethyl alcohol, Talc, Aerosil, Hydroxypropyl methyl cellulose, Eudragit, Polycoat, Triethyl citrate.

To obtain a formulation for topical administration, the components of the pharmaceutical composition include but are not limited to: isopropyl myristate, soy lecithin, pluronic 127, sorbic acid, potassium sorbate, cetyl alcohol, stearyl alcohol, stearic acid, triethanolamine, carbopol 940, carbopol 934, ethylenediamine tetraacetic disodium salt, sodium metabisulfite, propylene glycol, glycerin, heavy liquid petrolatum, methylparaben, propylparaben, polysorbate 80.

To obtain a controlled release topical formulation, the components of the pharmaceutical composition include but are not limited to: isopropyl myristate, soy lecithin, pluronic 127, sorbic acid, potassium sorbate, cetyl alcohol, stearyl alcohol, stearic acid, triethanolamine, carbopol 940, carbopol 934, ethylenediamine tetraacetic disodium salt, sodium metabisulfite, propylene glycol, glycerin, heavy liquid petrolatum, methylparaben, propylparaben, polysorbate 80, hydrogenated soy phosphatidylcholine, distearyl phosphatidyl glycerol, sodium salt, distearyl phosphatidyl choline, cholesterol, chitosan.

EXAMPLES

Example 1

Persistent Pain Model (Formalin Test, Acute Spontaneous Behavior)

The rats were placed individually in an open cylindrical glass chamber (34×30×28 cm). The animals had 20 minutes to get used to the camera before the injection and returned to it immediately after the injection for observation. An hour prior to the injection of formalin the animals were gently immobilized for oral administration by gavage of the drugs at different doses or their vehicle according to their assigned group. The formalin (50 µL, s.c.) was injected into the plantar region of the right hind paw of the rat using a microsyringe with a 26 G gauge needle. The licking/biting behavior of the injected paw was recorded using a digital timer as the total licking/biting time (s) for observation periods of 5 minutes for 45 minutes after the formalin injection. Response curves for formalin-induced licking/biting behavior were generated by the phase records: early (0-5 min), latency (5-15 min) and late or tonic (15-45 min). The data is presented as average time of licking/biting (/5 min/sec)±SEM during the 45 minutes of the test. At the end of the experiment the animals were sacrificed under diethyl ether atmosphere.

Example 2

Sciatic Nerve Chronic Constriction Injury Model (Neuropathic Surgery). Behavioural Assessment of Mechanical Allodynia and Mechanical Hypernociception Animals were anesthetized with thiopental (50 mg/kg, i.p.). A chronic constriction injury (CCI) was produced by ligating the common sciatic nerve on the left side (Bennett and Xie, 1988). Briefly, the common sciatic nerve was exposed at the level of the middle of the thigh by blunt dissection through the biceps femoris. Proximal to its trifurcation, about 7 mm of nerve was freed of adhering tissue and three ligatures (using 4.0 chromic gut) were tied loosely around it at 1-1.5 mm intervals. The ligatures just barely constricted the diameter of the nerve when viewed by 40× magnification. This degree of constriction retarded, but did not arrest, the circulation through the superficial epineural vasculature and produced a small, brief twitch in the muscle around the exposure. The incisions were closed in layers. In sham-operated controls, an identical operation was performed but without ligation of the sciatic nerve (Bennett, G. J. and Xie, Y. K. 1988. *Pain* 33:87-107).

The mechanical allodynia of the hind paw was evaluated by the withdrawal response of the paw before the stimulation of the von Frey filaments. Once the animals were placed in the test boxes (inverted plastic boxes with lids of 21×16× 27 cm3), the filaments were applied to the plantar surface of the leg (center) in ascending and descending order as necessary to close the response threshold. Each filament was applied 5 times, response 3 of 5 applications will be considered positive. The lowest stimulus intensity corresponded to 0.25 g and the maximum intensity to 15 g. Based on the response pattern and the strength of each filament, 50% of the response threshold in grams was calculated. The animal must have its four legs supported, resting on a metal mesh floor) can not be exploring or grooming at the time of measurement, the adaptation period of 5-10 minutes was completed. The resulting pattern of positive or negative response was tabulated using the conversion X=withdrawal 0=not withdrawn and 50% of the response threshold was interpolated using the formula: 50% g threshold=(10f [x+Kδ])/10,000, where xf=value (in Log units) of the final filament used, κ=tabular value for positive or negative pattern and 5=mean of differences between stimuli (in Log units), in this case 0.224 (Chaplan, S R et al., 1994. *J. Neurosci, Methods* 53: 55-63).

We proceeded in a similar way for the measurement of mechanical hypernociception, but the withdrawal response was measured with a von Frey electronic model INSIGHT®, Brazil. The test consists of the evocation of the withdrawal response by applying a manual force transducer of the electronic analgesiometer that has a polypropylene tip of 0.5 mm2. This is applied perpendicularly to the central plantar area of the hind paw with a gradual increase in strength. The leg is removed with a characteristic flinching; after the withdrawal the intensity of the pressure is recorded electronically. The value of the response is averaged over three measurements. The animal is evaluated before and after the treatments and the results are expressed as difference (Δ) of the withdrawal threshold in grams by subtraction of the mean of the measurements at the different time intervals from the mean of the measurements at time 0 (Cunha, T M et al., 2004. *Braz. J. Med. Biol. Res.* 37:401-407).

Example 3

Behavioral Safety Pharmacological Tests

In order to rule out signs of motor deterioration, sedation or catalepsy. The rotating rod or rota-rod test was executed. The apparatus consists of a bar with a diameter of 2.5 cm divided into 4 compartments. The bar rotated at a constant speed of 22 rpm and the time it took for the animals to fall from the bar was evaluated. The animals were evaluated 1 h after the supply. The cut-off time used was 60 seconds. In addition, the tone, posture, righting reflex, corneal, vital signs and general state of the animal were explored from 30 minutes to 3 hours post-administration of the drugs separately and the combination. The corneal and tympanic reflex were explored by the tip of a thin paper to stimulate the cornea or auditory canal and the rapid response of opening and closing of the eyes or the mobilization of the ears in normal animals was observed. The evaluation of the posture and the righting reflex was based on the scale of Devor and Zalkind. Scale for posture: 0=normal posture, grooming supported on its hind legs; 1=moderate atony and ataxia, supports its weight, but can not rest on its hind legs; 2=supports its weight, but ataxia is severe; 3=maintains muscle tone, but can not support its weight, only small movements of intention; 4=atony, flaccidity, totally immobilized, no efforts to mobilize. Scale for righting reflex: 0=the rat struggles when placed horizontally on its back on a table followed by a quick, coordinated and powerful reincorporation; 1=Moderate resistance when placed on its back with quick but not powerful reincorporation; 2=there is no resistance when placed on its back, with effort, but finally successful reincorporation; 3=unsuccessful reincorporation; 4=no movements (Rosland, J. H. et al., 1990. *Pharmacol, Toxicol.* 66: 382-6, Devor, M. and Zalkind, V. 2001. *Pain* 94: 101-112).

Example 4

Pharmacological Interaction Study. Isobolographic Analysis

The method is based on the selection of an effect level that is usually 50% of the maximum effect (ED50%). If this effect is not produced, the ED30 is used. These effects are obtained from the corresponding dose-response curves of each drug administered in 4 doses to the animals. An additive combination corresponding to the determined effect is constituted by 2 parts that contribute a fraction of said effect. In this case it was selected that each fraction was 0.5 so that the theoretical ED50 (ED50T) of the combination contains 0.5 of the ED50 of amitriptyline and 0.5 of the ED50 of paracetamol. Subsequently an experimental dose-response curve is created that contains combinations at the established ratio (ED50T) 1/2, 1/4, 1/8 and 1/16 and the experimental ED is calculated, which is compared statistically with the theoretical one. The isobologram shows the results on a graph whose coordinates represent the contribution of each drug. The line that connects as intercepts to the ED50 of paracetamol and amitriptyline contains all the possible additive combinations (line of simple additivity) and the center of this line corresponds to the ED50T of the combination or point of additivity (Tallarida, R J 2011. *Genes and Cancer* 10: 1003-1008; Raffa, R B et al., 2010. *J. Pain* 11: 701-709). The resulting ED50E experimental point is plotted in the Cartesian coordinate system and the region where it is located determines the type of interaction. In the case that the interaction is synergistic, the experimental point is located under the line of additivity. In the opposite case, if an antagonistic interaction results, the point will be located on the line of additivity and if the point is located in a sector close to the line of additivity, the interaction will be simple additivity. In addition, the interaction index between the drugs is calculated according to the following formula: ED50E/ED50T. If the resulting value is less than 1, it corresponds to a synergistic interaction; when it is equal to 1, the interaction is additive, and if it is greater than 1, it is antagonistic. The statistical analysis of the data obtained in the log dose response curves was analyzed by linear regression by minimum squares to determine the ED50 or ED30. The statistical parameters related to the isobolograms were calculated with a computer program of the Department of Pharmacobiology of the Center for Research and Advanced Studies, South Headquarters, Mexico City. The dose-response curves data were compared with their respective controls by one-way analysis of variance (ANOVA) followed by the Tukey or Dunnett test to compare the differences with the different treatments. The statistical significance between the ED50/30T and the ED50/30E was determined by the Student's t test, considering in all cases the significance at a level of 5% ($p<0.05$) (Argüelles, C F et al., 2002). *Anesthesiology* 96: 921-5; Caram-Salas, N L et al., 2006. *Pharmacology* 77:53-62).

Example 5

Histopathological Study

The animals were sacrificed at 14 days post-CCI by overdose of diethyl ether and samples of 5 mm sciatic nerve located distal to the lesion were stored in the fixative solution (10% formalin) and cut into 4 μm thickness. Staining was carried out by using hematoxylin and eosin. Nerve sections were analyzed qualitatively under light microscope (20×) for axonal degeneration induced by CCI. We proceeded in a similar way with the sciatic nerve sections of the sham operated animals. Animals treated with vehicle show increased relative cellularity with respect to the fake animals operated as a result of Schwann cell proliferation and macrophage infiltration, the presence of digestion chambers in Schwann cells with myelin ovoids, alignment disordered axons with loss of their myelin sheaths indicators of Wallerian degeneration. Qualitatively, the animals treated with the GBP as a positive control show a decrease in these alterations. The samples were taken from animals treated with the increasing doses of independent drugs and those of the combination (Sudoh, Y. et al., 2004. *Reg. Anesth. Pain Med.* 29: 434-40; Debovf, P. 2011. *Annals. of Anatomy* 193:267-275).

The invention claimed is:
1. A pharmaceutical composition comprising an active ingredient consisting of a fixed-dose combination of amitriptyline and paracetamol, wherein amitriptyline is present in an amount between 1-22.5 mg and paracetamol is present in an amount between 49-227.5 mg; and a pharmaceutically acceptable excipient for the immediate release of amitriptyline and paracetamol.
2. The pharmaceutical composition according to claim 1, wherein the composition is for oral, intranasal, topical, transdermal or intravenous administration.

3. The pharmaceutical composition according to claim 1, wherein the composition is in the form of a tablet, nasal spray, powder for inhalation, ointment, patch, solution or suspension for infusion.

4. A method of treatment or prevention of mixed cancer pain, said method comprising the administration to a subject in need thereof, a therapeutically effective dose of the pharmaceutical composition of claim 1.

5. The method according to claim 4, wherein the cancer pain is a mild pain.

6. The method according to claim 4, said method further comprising the administration of weak opioids in the prevention and/or treatment of mild to moderate pain.

7. The method according to claim 4, said method further comprising the administration of strong opioids in the prevention and/or treatment of moderate to severe pain.

8. The method according to claim 4, wherein said administration induces neuroprotection in neurodegeneration processes that accompany neuropathic pain syndromes in oncological and non-oncological diseases.

9. The method according to claim 4, wherein the method comprises the administration of the pharmaceutical composition one or more times per day.

10. The method according to claim 4, wherein the pharmaceutical composition is administered orally, topically, transdermally or intranasally.

11. The pharmaceutical composition according to claim 1, wherein the pharmaceutically acceptable excipients for the immediate release of amitriptyline and paracetamol are carboxymethyl sodium starch, polyvinylpyrrolidone K-25, or combinations thereof.

* * * * *